(12) United States Patent
Basu et al.

(10) Patent No.: US 9,089,406 B2
(45) Date of Patent: Jul. 28, 2015

(54) EMBOLIC FILTER DEVICES, SYSTEMS, AND METHODS FOR CAPTURING EMBOLI DURING MEDICAL PROCEDURES

(71) Applicant: THE CLEVELAND CLINIC FOUNDATION, Cleveland, OH (US)

(72) Inventors: Shubhayu Basu, Solon, OH (US);
Stephen Ellis, Beachwood, OH (US);
Dave Dudzinski, Lakewood, OH (US);
Ryan S. Klatte, Fairview Park, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/756,813

(22) Filed: Feb. 1, 2013

(65) Prior Publication Data
US 2013/0245669 A1    Sep. 19, 2013

Related U.S. Application Data

(60) Provisional application No. 61/594,517, filed on Feb. 3, 2012, provisional application No. 61/708,180, filed on Oct. 1, 2012.

(51) Int. Cl.
*A61F 2/01* (2006.01)

(52) U.S. Cl.
CPC . *A61F 2/013* (2013.01); *A61F 2/01* (2013.01); *A61F 2002/011* (2013.01); *A61F 2230/005* (2013.01); *A61F 2230/0008* (2013.01); *A61F 2230/0015* (2013.01)

(58) Field of Classification Search
USPC .......... 606/194, 200, 191; 623/1.11, 2.11
See application file for complete search history.

(56) References Cited

U.S. PATENT DOCUMENTS

| 5,895,399 | A | * | 4/1999 | Barbut et al. | 606/159 |
| 6,129,739 | A | | 10/2000 | Khosravi | |
| 2004/0204737 | A1 | * | 10/2004 | Boismier et al. | 606/200 |
| 2006/0149295 | A1 | | 7/2006 | Fleming, III | |
| 2006/0287668 | A1 | * | 12/2006 | Fawzi et al. | 606/200 |
| 2012/0172920 | A1 | * | 7/2012 | Fifer et al. | 606/200 |

FOREIGN PATENT DOCUMENTS

| WO | 9855175 A1 | 12/1998 |
| WO | 2010077949 A1 | 7/2010 |

OTHER PUBLICATIONS

PCT International Search Report, PCT/US2013/024299, mailed Apr. 23, 2013, pp. 1-12.

* cited by examiner

*Primary Examiner* — Alexander Orkin
(74) *Attorney, Agent, or Firm* — Tarolli, Sundheim, Covell & Tummino LLP

(57) ABSTRACT

One aspect of the present disclosure relates to an embolic filter device configured for placement in a blood vessel to capture emboli during a medical procedure. The embolic filter device can include an expandable frame member and a membrane. The expandable frame member can include a radial support member operably connected to first and second longitudinal struts, and an engaging portion extending between the first and second longitudinal struts. The engaging portion can be shaped and configured to temporarily receive, and sealingly mate with, a portion of an endovascular catheter during the medical procedure. The membrane can be securely connected to the frame member and define a collection chamber for captured emboli. The membrane can be configured to cover substantially all of the cross-sectional area of the blood vessel when the embolic filter device is deployed in the blood vessel.

17 Claims, 41 Drawing Sheets

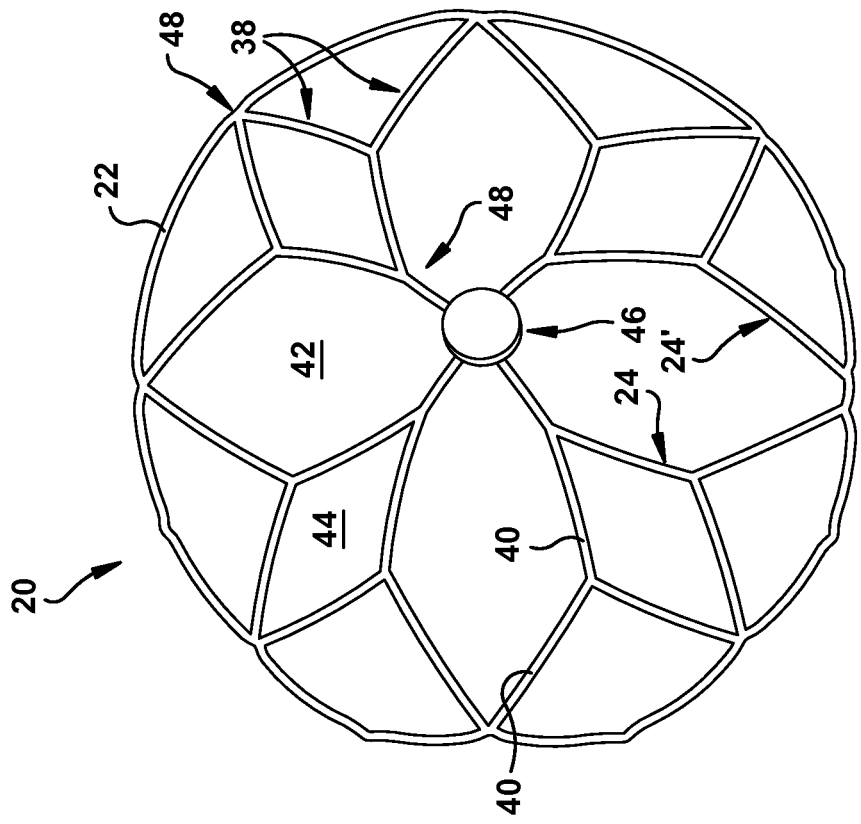
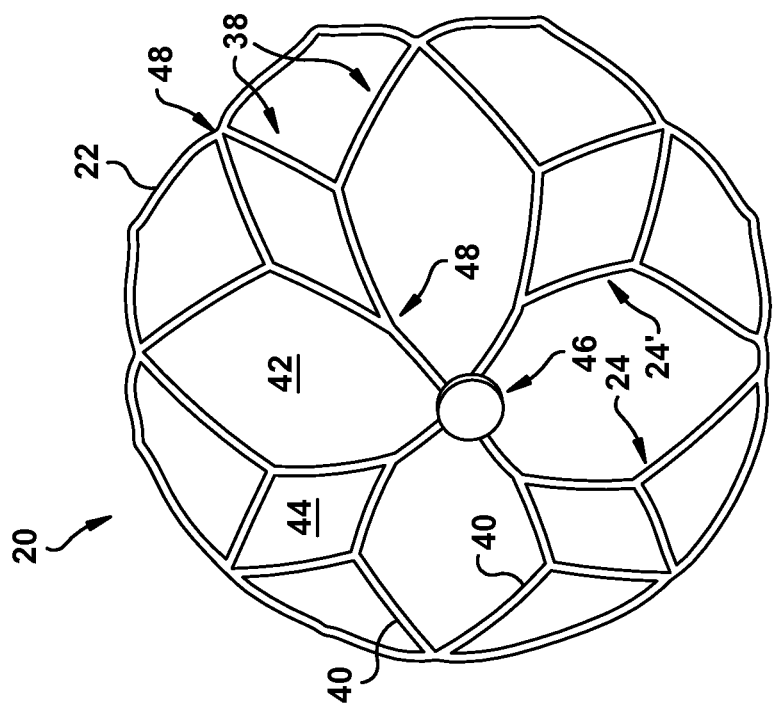

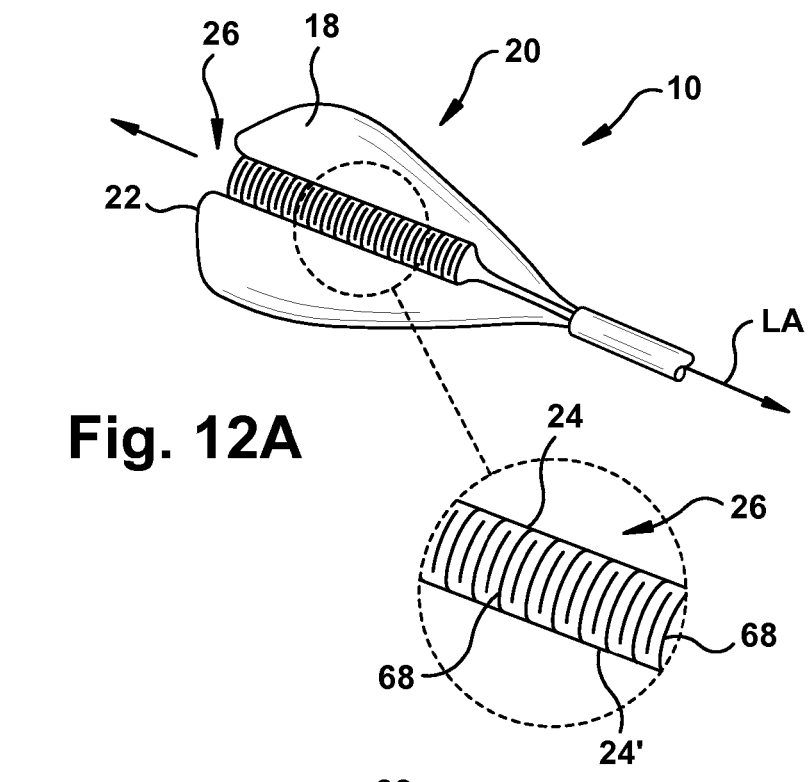
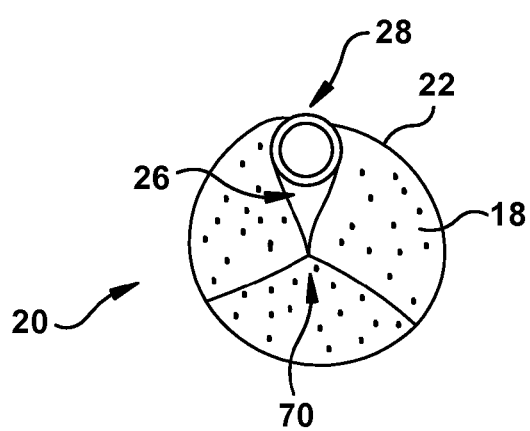
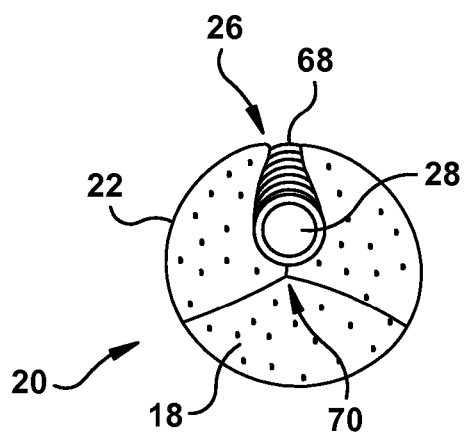
Fig. 12A
Fig. 12B
Fig. 12C

EMBOLIC FILTER DEVICES, SYSTEMS, AND METHODS FOR CAPTURING EMBOLI DURING MEDICAL PROCEDURES

RELATED APPLICATIONS

This application claims the benefit of U.S. Provisional Patent Application Ser. Nos. 61/594,517, filed Feb. 3, 2012, and 61/708,180, filed Oct. 1, 2012, the entirety of each of which is hereby incorporated by reference for all purposes.

TECHNICAL FIELD

The present disclosure relates generally to devices and methods for providing embolic protection in the vasculature of a subject, and more particularly to embolic filter devices that can be deployed in a subject's aorta to protect aortic arch vessels and downstream organs from potential emboli.

BACKGROUND

Cerebral embolism is a known complication of cardiac surgery, cardiopulmonary bypass, and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Other sources of potential emboli include cardiogenic emboli, such as thrombus that results from chronic atrial fibrillation and emboli from ruptured or vulnerable aortic plaque. Cerebral embolism can lead to neuropsychological deficits, stroke and even death. Other organs downstream can also be damaged by embolism, resulting in diminished function or organ failure.

SUMMARY

One aspect of the present disclosure relates to an embolic filter device configured for placement in a blood vessel to capture emboli during a medical procedure. The embolic filter device can comprise an expandable frame member and a membrane. The expandable frame member can include a radial support member operably connected to first and second longitudinal struts, and an engaging portion extending between the first and second longitudinal struts. The engaging portion can be shaped and configured to temporarily receive, and sealingly mate with, a portion of an endovascular catheter during the medical procedure. The membrane can be securely connected to the frame member and define a collection chamber for captured emboli. The membrane can be configured to cover substantially all of the cross-sectional area of the blood vessel when the embolic filter device is deployed in the blood vessel.

Another aspect of the present disclosure relates to an intravascular system for capturing emboli during a medical procedure. The intravascular system can comprise an embolic filter device and a multi-lumen delivery catheter. The embolic filter device can comprise an expandable frame member and a membrane. The expandable frame member can include a radial support member operably connected to first and second longitudinal struts, and an engaging portion extending between the first and second longitudinal struts. The engaging portion can be shaped and configured to temporarily receive, and sealingly mate with, a portion of an endovascular catheter during the medical procedure. The membrane can be securely connected to the frame member and define a collection chamber for captured emboli. The multi-lumen delivery catheter can have a plurality of lumens, at least one of which can be configured to deploy the embolic filter device.

Another aspect of the present disclosure relates to a method for capturing emboli during a medical procedure. One step of the method can include providing an embolic filter device and a multi-lumen delivery catheter. The embolic filter device can comprise an expandable frame member and a membrane. The expandable frame member can include a radial support member operably connected to first and second longitudinal struts, and an engaging portion extending between the first and second longitudinal struts. The engaging portion can be shaped and configured to temporarily receive, and sealingly mate with, a portion of an endovascular catheter during the medical procedure. The membrane can be securely connected to the frame member and define a collection chamber for captured emboli. Next, the multi-lumen delivery catheter can then be advanced to a deployment site in a blood vessel that is proximate a target location. The endovascular catheter can then be advanced to the target location. The embolic filter device can be deployed from the multi-lumen delivery catheter at the deployment site so that the engaging portion is sealingly wrapped around a portion of the endovascular catheter and the membrane covers substantially all of the cross-sectional area of the blood vessel. The medical procedure can then be conducted.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 8A-B are front views showing an alternative configuration of an expandable frame member comprising the embolic filter device in FIGS. 1A-B;

FIG. 12A is a perspective view showing an alternative configuration of the embolic filter device in FIG. 11C;

FIGS. 12B-C are front views showing an endovascular catheter mated with the embolic filter device in FIG. 12A;

DETAILED DESCRIPTION

Figure 1A:
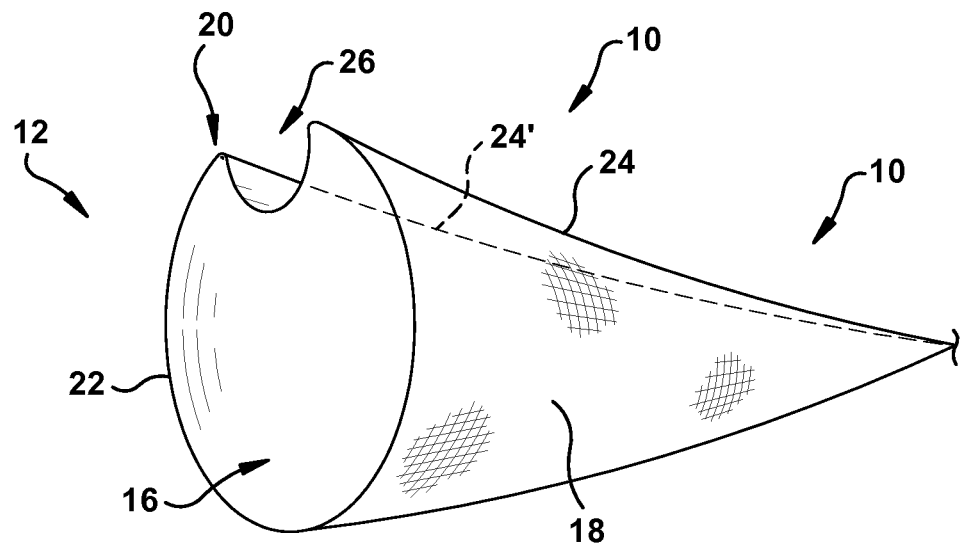
FIG. 1A is a perspective view of an embolic filter device constructed in accordance with one aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures.

It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

Figure 1B:
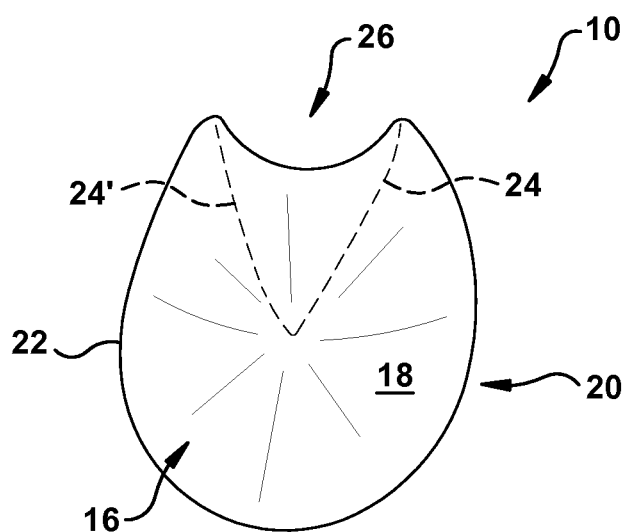
FIG. 1B is a front view of the embolic filter device in FIG. 1A.

The present disclosure relates generally to devices and methods for providing embolic protection in the vasculature of a subject (e.g., a human), and more particularly to embolic filter devices that can be deployed in a subject's aorta to protect aortic arch vessels and downstream organs from potential emboli. As representative of one aspect of the present disclosure, FIGS. 1A-B illustrate an embolic filter device 10 configured for placement in a blood vessel to capture emboli during a medical procedure. Although the present disclosure is described primarily in terms of preventing emboli from entering the cerebral or peripheral circulation during and/or after transcatheter valve implantation (TAVI), one skilled in the art will appreciate that the present disclosure can be employed in any medical procedure where there is a potential risk of emboli traveling to downstream organ systems (e.g., catheter-based or interventional procedures, such as mitral valve replacement). For example, devices and system of the present disclosure can be deployed in a subject to prevent or reduce of stroke, silent stroke, and other embolic events in the brain, gut and kidneys and the peripheral vasculature during or after surgical, minimally invasive and percutaneous procedures, including, but not limited to transcatheter aortic valve replacement procedures.

Devices and methods for preventing emboli during medical procedures, such as cardiovascular interventions are known in the art. Many of these devices merely deflect emboli from entering critical vasculature and, moreover, fail to capture and prevent potentially lethal emboli from lodging in vital downstream organs. Of the devices that do capture emboli, the devices do so in specific vessels and do not protect the overall vasculature, e.g., downstream of the ascending aorta. Additionally, many of these devices are deployed separately from a pigtail catheter, which is used to introduce radio-opaque contrast for implant (e.g., a prosthetic aortic valve) confirmation. The pigtail catheter is critical for positioning and placement of an implant as, for example, a physician loses the means to introduce radio-opaque contrast once the pigtail catheter is removed.

As described in more detail below, the present disclosure is advantageously deployed in the ascending aorta and provides embolic filter devices, systems, and methods that: (1) actually capture emboli without merely deflecting emboli into the peripheral circulation; (2) comprise a modified multi-lumen delivery catheter that enables both embolic filter device deployment and radio-opaque contrast delivery without the need for an additional access site over standard procedures; (3) when used for TAVI, allow for device placement in the ascending aorta to protect all three aortic branch vessels (i.e., the brachiocephalic artery, the left common carotid artery, and the left subclavian artery), as well as the descending aorta by mating with a portion of the endovascular catheter (e.g., the main TAVI catheter) and covering the cross-sectional area of the ascending aorta instead of merely covering the ostia of the aortic branch vessels; (4) allow continued adjustment and maneuverability of an endovascular catheter without increasing the risk of emboli lodging in downstream organs; and (5) include various mechanisms for quickly and efficiently capturing an endovascular catheter, as well as ensuring that substantially all of the cross-sectional area of a blood vessel is covered during a medical procedure.

Devices

One aspect of the present disclosure is illustrated in FIGS. 1A-B and includes an embolic filter device 10 configured for placement in a blood vessel to capture emboli during a medical procedure. FIG. 1A shows the embolic filter device 10 in a deployed configuration. In the deployed configuration, the embolic filter device 10 has an approximately conical configuration. The embolic filter device 10 includes a first open end 12 that is open to blood flow, and a second closed end 14 configured to capture emboli. As described in more detail below, the portion of the embolic filter device 10 extending between the first open end 12 and the second closed end 14 defines a collection chamber 16 for capturing emboli.

The embolic filter device 10 is comprised of a membrane 18 and an expandable frame member 20 that allows the embolic filter device to be self-supporting in the deployed configuration. The frame member 20 includes a radial support member 22 that is securely and directly connected to at least one longitudinal strut 24. As shown in FIG. 1A, the frame member 20 includes first and second longitudinal struts 24 and 24', each of which is securely and directly attached to the radial support member 22. Alternatively, the frame member 20 can include four, non-linear or wave-like struts 24 (FIG. 3B) that allow for gradual or staged deployment of the embolic filter device 10.

The frame member 20 has a generally wire-like or filamentous configuration. The frame member 20 can be made of a resilient material (e.g., stainless steel, Nitinol and/or polymer) that impart(s) the frame member, and thus the embolic filter device 10, with the ability to self-expand. Alternatively, the frame member 20 can be made of a shape-memory material to facilitate deployment and/or withdrawal of the embolic filter device 10 from the vasculature of a subject.

Figure 2A:
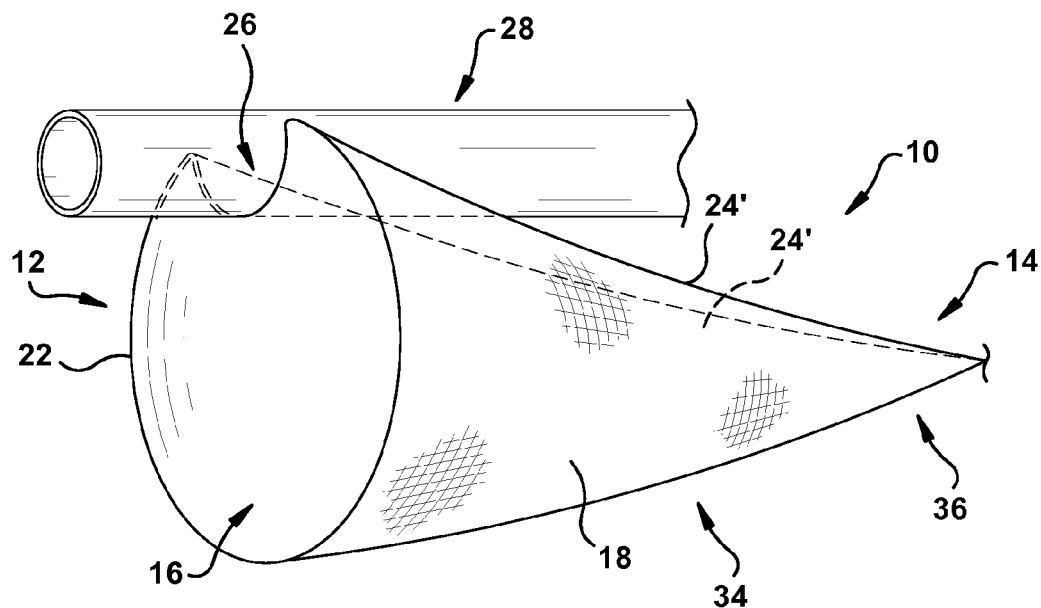
FIG. 2A is a perspective view showing an engaging portion of the embolic filter device in FIGS. 1A-B sealingly mated with a portion of an endovascular catheter.
Figure 2B:
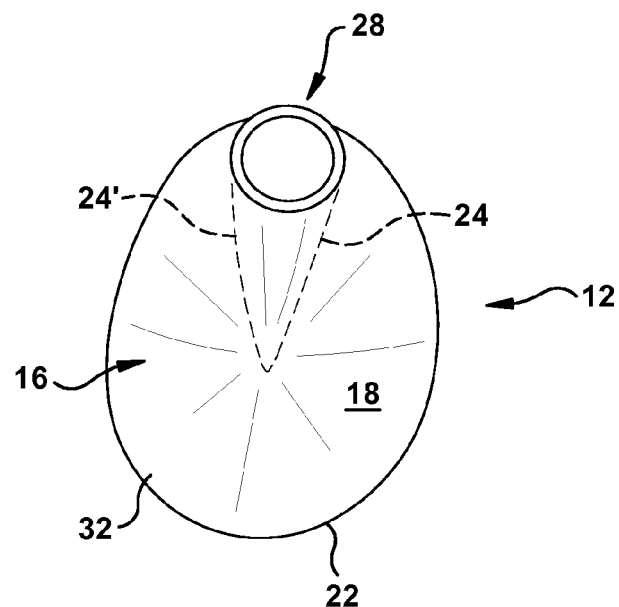
FIG. 2B is a front view of the embolic filter device and endovascular catheter in FIG. 2A.
Figure 3A:
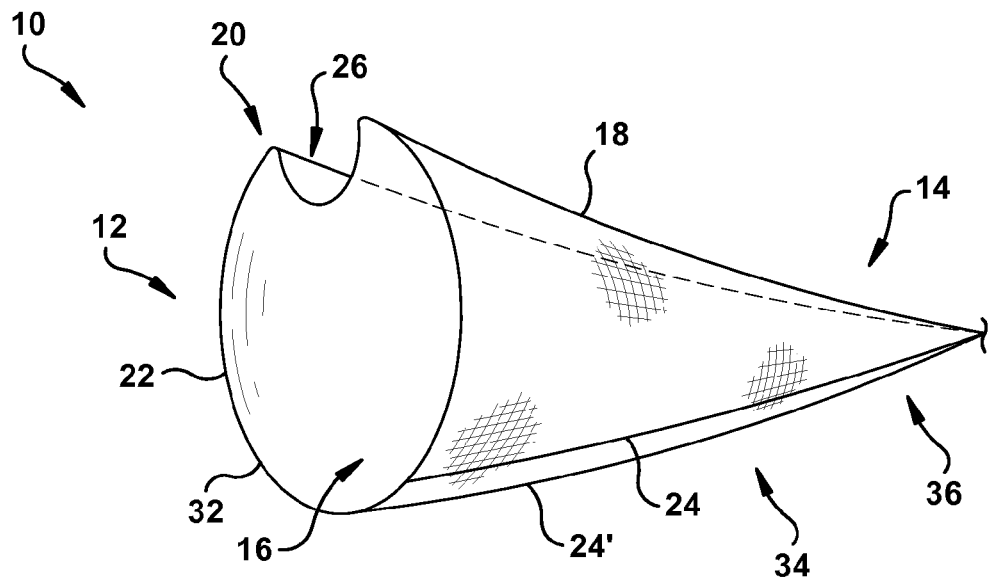
FIG. 3A is a perspective view showing an alternative configuration of the embolic filter device in FIGS. 1A-B.
Figure 3B:
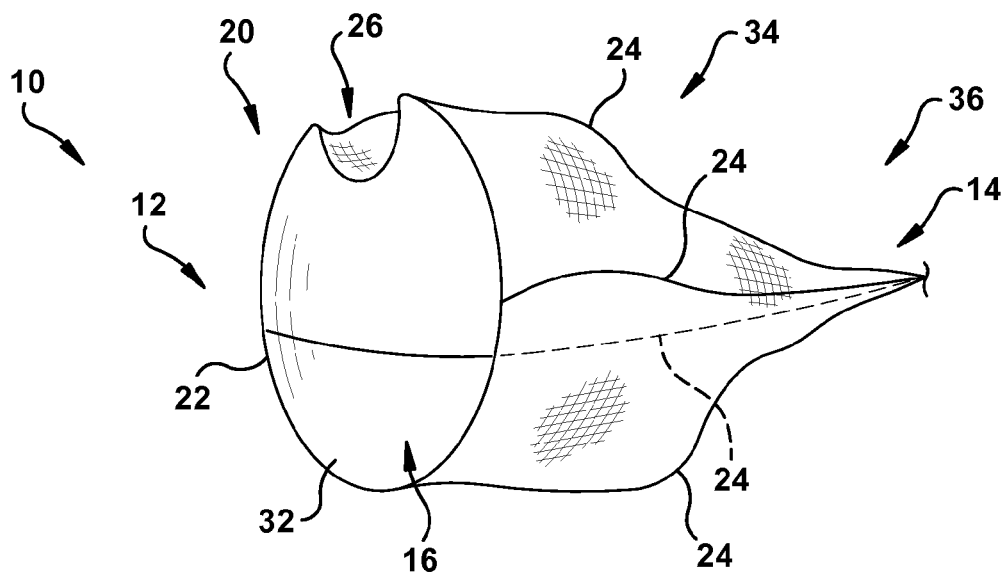
FIG. 3B is a perspective view showing an alternative configuration of the embolic filter device in FIGS. 1A-B.

The radial support member 22 includes, at least in part, an engaging portion 26 that is shaped, dimensioned, and sized to temporarily receive, and sealingly mate with, an outer wall portion of an endovascular catheter 28 during a medical procedure (FIGS. 2A-B). As discussed more below, the engaging portion 28 advantageously imparts the embolic filter device 10 with a "notch-like" structure that allows the medical procedure to be conducted without disruption (e.g., deploying and withdrawing multiple different catheters and filters at different stages of the procedure). It will be appreciated that the engaging portion 26 need not make a perfect hemostatic seal with the endovascular catheter 28; rather, the only requirement is that the engaging portion should sealingly mate with the endovascular catheter to exclude the passage of emboli above a certain size. The engaging portion 26 extends radially between the first and second longitudinal struts 24 and 24'. As shown in FIG. 1A, the engaging portion 26 has a crescent shape adapted to mate with the outer wall portion of the endovascular catheter 28. It will be appreciated, however, that the engaging portion 26 can have any shape and configuration sufficient to sealingly mate with an endovascular catheter 28. Thus, the engaging portion 26 can be sized and dimensioned to accommodate a range of endovascular catheter sizes. The engaging portion 26 is also sized and configured so that movement of an endovascular catheter 28 across the embolic filter device 10 will not jostle or dislodge the embolic filter device. Alternative configurations of the engaging portion 26, as well as other components of the embolic filter device 10 are described below. As shown in FIG. 3A, for example, the first and second longitudinal struts 24 and 24' can be disposed on opposite ends of the engaging portion 26.

The engaging portion 26 is continuous with the remainder of the radial support member 22. The perimeter of the radial support member 22 is generally circular, except for the engaging portion 26. In some instances, the radius of curvature of the engaging portion 26 can be equal, or about equal to, the radius of curvature of a portion of an endovascular catheter 28 with which the engaging portion is temporarily mated. For example, the engaging portion 26 can have a pre-determined radius of curvature (e.g., based on a known radius of curvature of the endovascular catheter 28). Alternatively, the engaging portion 26 can have a radius of curvature that is different than the radius of curvature of the endovascular catheter 28, but can obtain a radius of curvature that his substantially similar to the radius of curvature of a portion of the endovascular catheter with which the engaging portion is temporarily mated. As described in more detail below, the portion of the radial support member 22 that does not comprise the engaging portion 26 is sized and configured to make a seal with a luminal surface of a blood vessel upon deployment so that blood flow will be directed into the collection chamber 16 to capture any emboli.

Figure 4:
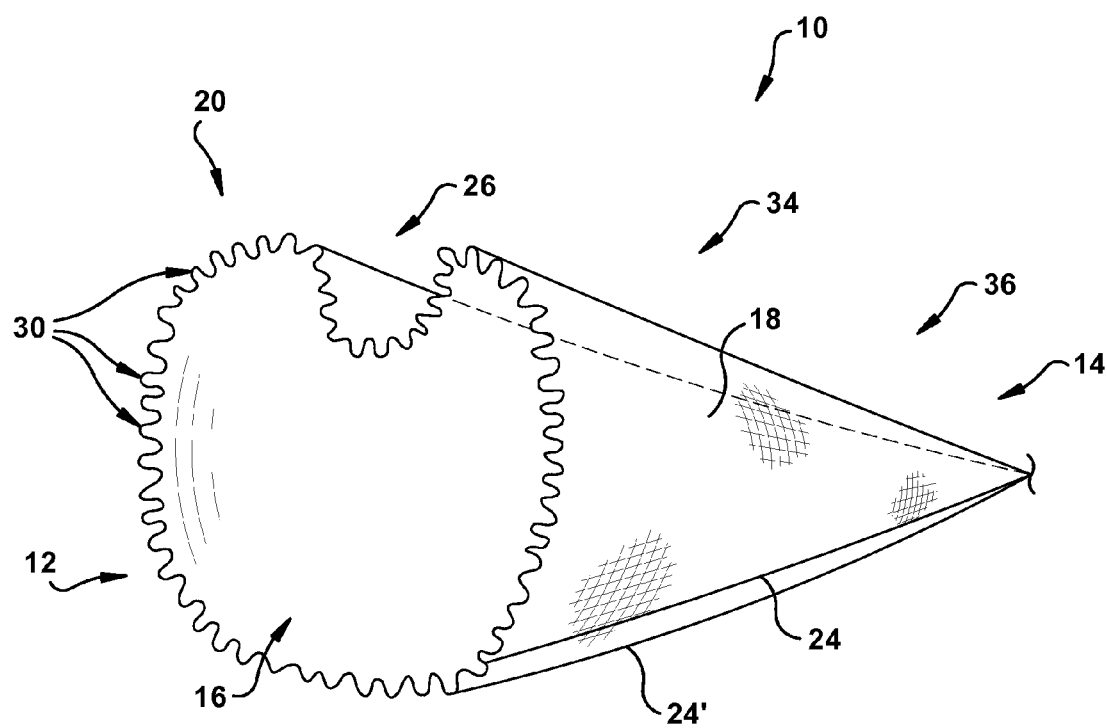
FIG. 4 is a perspective view showing an alternative configuration of the embolic filter device in FIG. 3A.
Figure 5A:
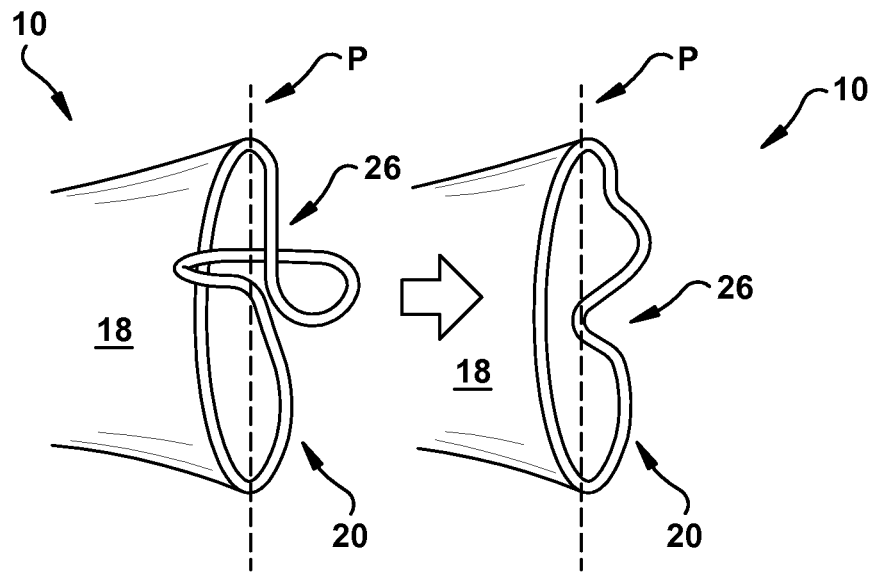
FIG. 5A is a perspective view showing an alternative configuration of a frame member comprising the embolic filter device in FIGS. 1A-B.
Figure 5B:
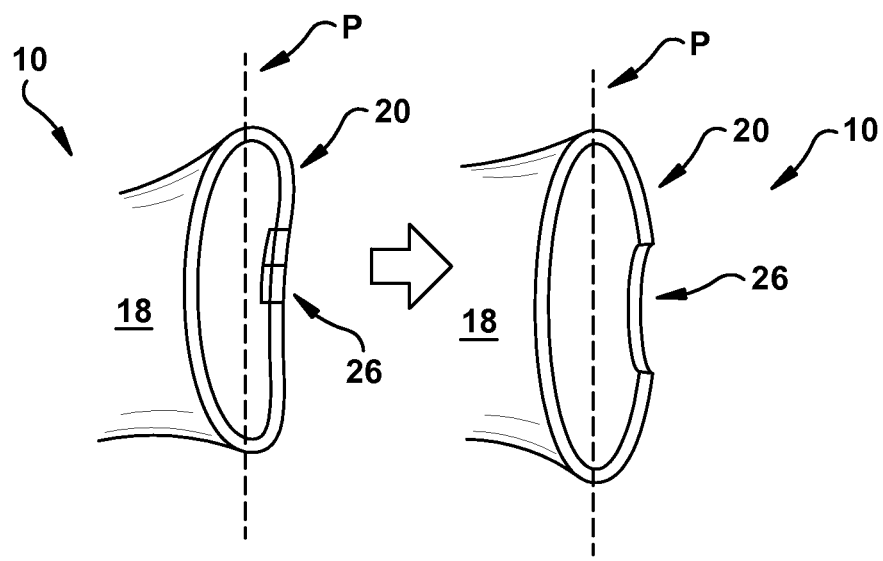
FIG. 5B is a perspective view showing an alternative configuration of the frame member in FIG. 5A.
Figure 6:
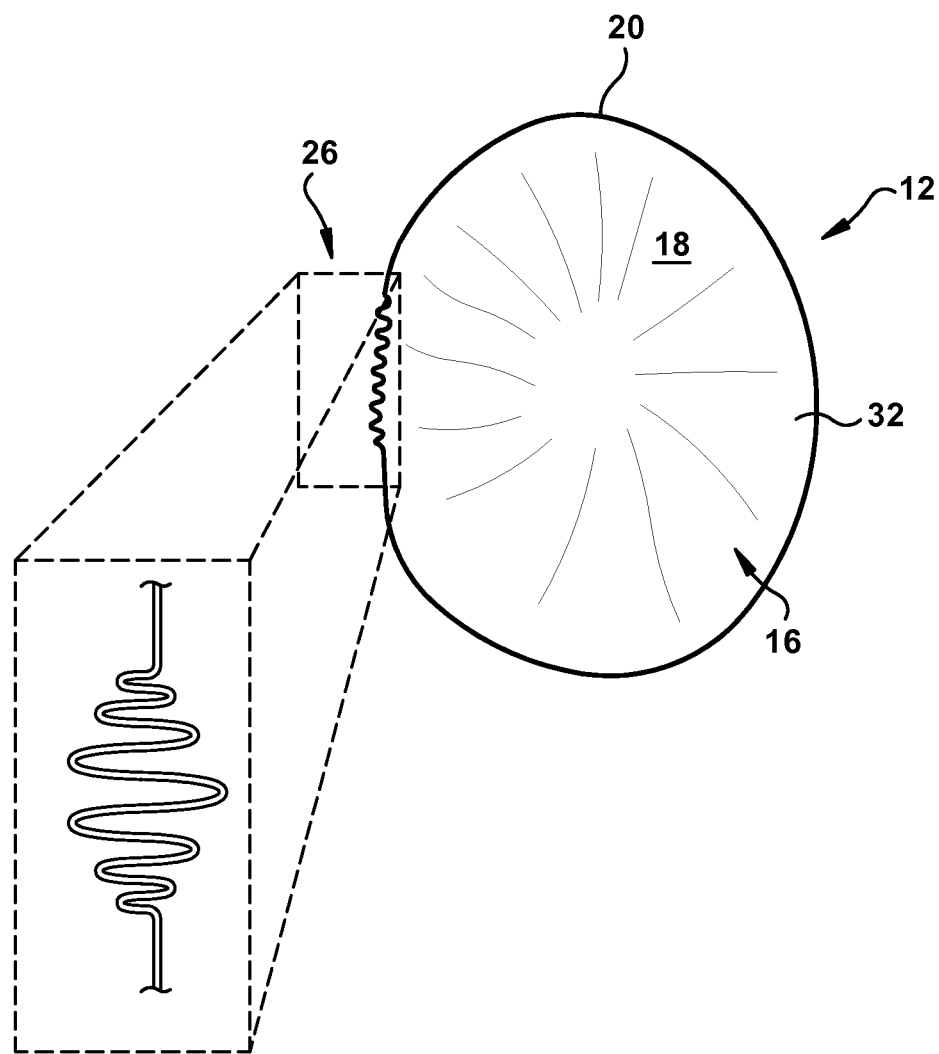
FIG. 6 is a perspective view of a magnified section of the embolic filter device in FIG. 1B showing an alternative construction of the engaging portion.

Alternative configurations of the radial support member 22 are shown in FIGS. 4-6. As shown in FIG. 4, for example, all or only a portion of the radial support member 22 can comprise a repeating series of single-width cells 30 to increase the radial force of the radial support member. The engaging portion 26 can extend substantially perpendicular to a vertical plane P defined by the diameter of the radial support member 22 (FIG. 5A) or, alternatively, the engaging portion can extend substantially parallel to the vertical plane P as shown in FIG. 5B. The engaging portion 26 can additionally or optionally comprise a series of periodic waves (FIG. 6) to locally weaken the radial stiffness of the engaging portion and facilitate deformation of the engaging portion about the endovascular catheter 28.

As noted above, the embolic filter device 10 (FIGS. 1A-B) comprises a membrane 18 that is securely and directly connected to the frame member 20, which defines a collection chamber 16 for captured emboli. The membrane 18 is supported by the frame member 20 and can be resilient, flaccid, or plastically deformable. The membrane 18 includes a distal peripheral edge 32 that is securely connected to a peripheral edge (not shown in detail) of the radial support member 22. Additionally, a body portion 34 of the membrane 18 is supported by, and connected to, at least one longitudinal strut 24. A distal end 36 of the membrane 18 forms the second closed end 14 of the embolic filter device 10. The membrane 18 is configured to cover substantially all of the cross-sectional area of a blood vessel when the embolic filter device 10 is deployed in the blood vessel.

The membrane 18 can be made of a porous, filter mesh material (e.g., nylon, polyurethane, PTFE, ePTFE) having a pore size chosen to stop emboli above a certain size from passing therethrough. For example, the membrane 18 can be made of a metal and/or polymer formed into knitted, woven or nonwoven fiber(s), filament(s) or wire(s). The material comprising the membrane 18 can have a pore size in the range of approximately 1 mm to 0.1 mm or even smaller, depending on whether the embolic filter device 10 is intended to capture macroemboli only or microemboli as well. It will be appreciated that a portion of the membrane 18 can alternatively be constructed of an impermeable material rather than a porous, filter mesh material.

In some instances, the membrane 18 can include a first portion having a first elasticity that is different than an elasticity of a second different portion of the membrane. For example, a portion of the membrane 12 at or near the first open end 12 can have an elasticity that is greater than the elasticity at or near the second closed end 14. Such a configuration may be ideal for accommodating the movement/motion at the first open end 12 of the membrane 18 during use of the embolic filter device 10. In such instances, the membrane 18 may be made of a single material having two or more portions with a different respective elasticity. Alternatively, the membrane 18 may be made of two or more different materials, each of which can have a different elasticity. In other instances, it will be appreciated that the membrane 18 can have a uniform or asymmetrical pore distribution and, further, that the membrane can include pores of the same or varying diameters.

Figure 7A:
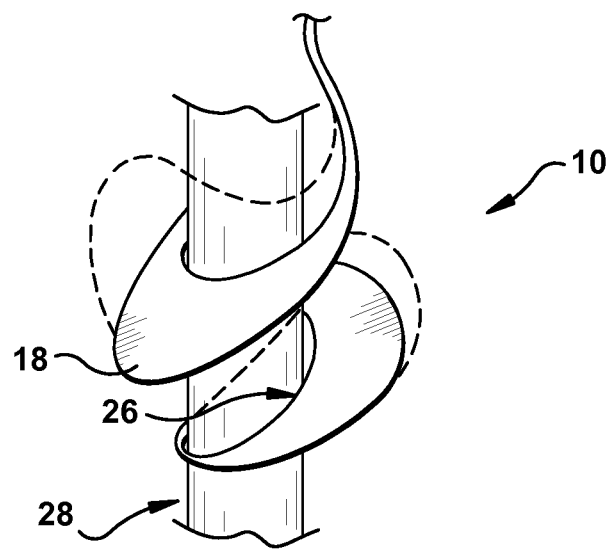
FIG. 7A is a perspective view showing an alternative configuration of the embolic filter device in FIGS. 1A-B constructed in accordance with another aspect of the present disclosure.
Figure 7B:
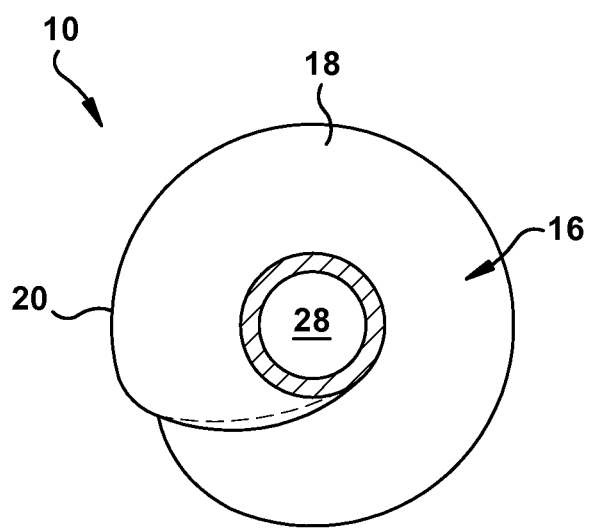
FIG. 7B is a front view of the embolic filter device in FIG. 7A.

FIGS. 7A-B illustrate another alternative configuration of the embolic filter device 10. In some instances, the embolic filter device 10 can have a spiral-shaped configuration in the deployed configuration. In this configuration, an S-shaped frame member 20 includes multiple engaging portions 26 that are each sized and configured to sealingly mate with respective portions of an endovascular catheter 28. When the embolic filter device 10 is deployed about an endovascular catheter 28 (as shown in FIG. 7B), a seal is formed therebetween that excludes the passage of emboli between the frame member 20 and the endovascular catheter. Similarly, the portion of the frame member 20 that is not in contact with the endovascular catheter 28 makes a seal with the vessel luminal wall so that blood flow is directed into a collection chamber 16 formed by a membrane 18 to capture emboli.

Figure 8C:
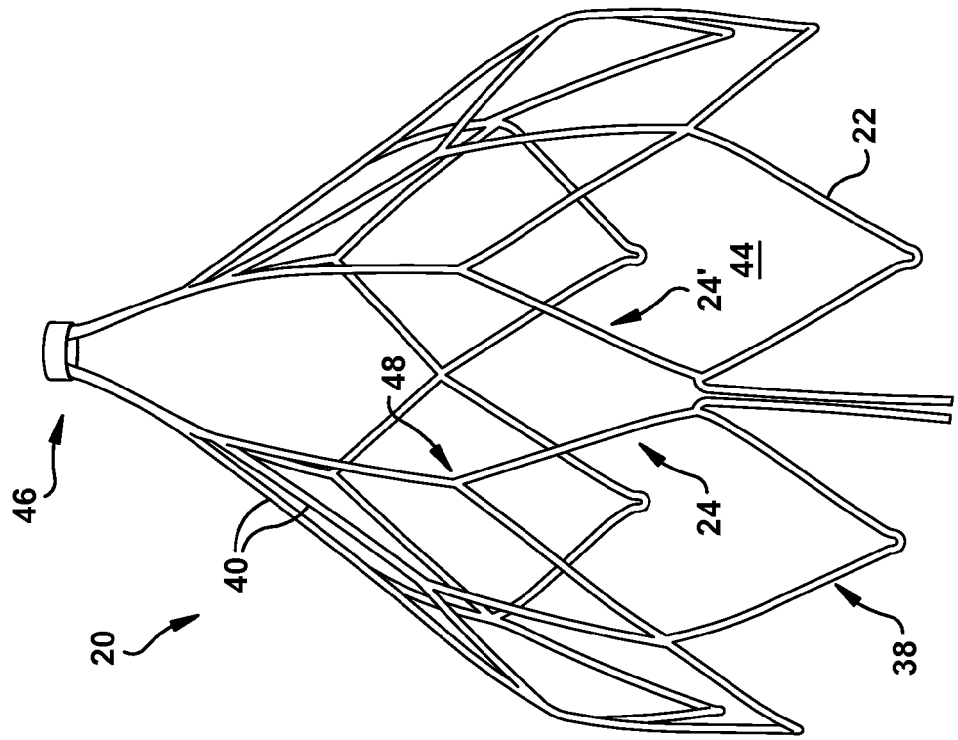
FIGS. 8C-D are side views of the expandable frame member in FIGS. 8A-B.

In another aspect, alternative configurations of the expandable frame member 20 are illustrated in FIGS. 8A-B and FIGS. 8C-D. The frame member 20 in FIGS. 8A-B is identically constructed as the frame member in FIGS. 8C-D, save that the radial support member 22 in FIGS. 8A-B has a substantially O-shaped circular configuration, whereas the radial support member in FIGS. 8C-D has a Z-shaped configuration. Although not shown, it will be appreciated that each frame member 20 can include a membrane 18 securely affixed thereto. Additionally, each frame member 20 includes first and second longitudinal struts 24 and 24', which, as described below, can be comprised of one or more longitudinally extending filaments 40. Although the engaging portion 26 is generally defined by first and second longitudinal struts 24 and 24', it will be appreciated that one or more filaments 40 can extend (e.g., radially) between the longitudinal struts to provide further radial support for the frame member 20.

Figure 8D:
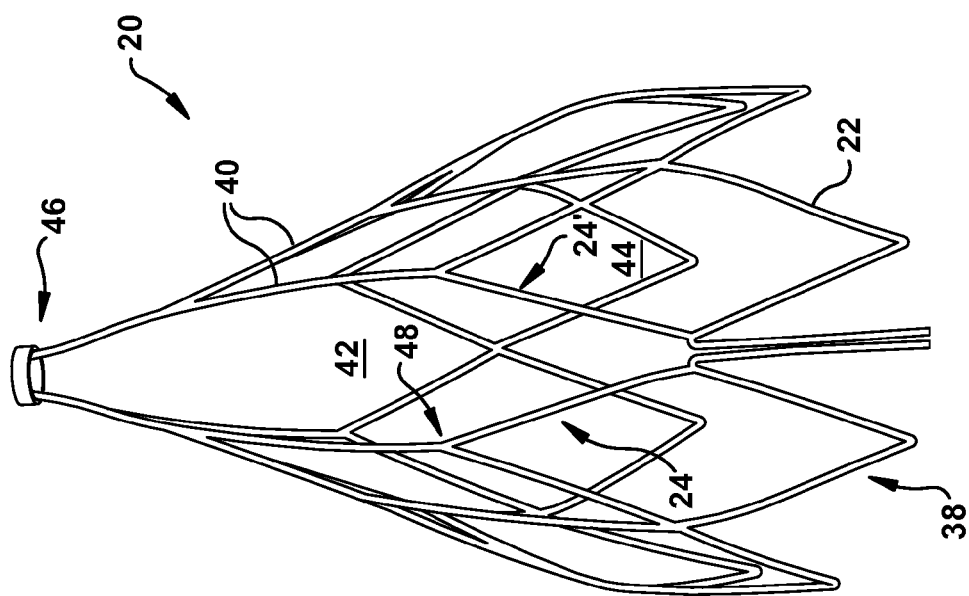

As shown in FIGS. 8A-D, the frame member 20 can comprise one or more diamond-shaped cells 38. Each of the diamond-shaped cells 38 can include a plurality of flexible filaments 40 integrally formed with one another. In some instances, each of the diamond-shaped cells 38 is defined by the radial support member 22 (e.g., having a Z-shaped configuration) and a series of filaments 40 having a Y-shape. In other instances, the expandable frame member 20 can comprise one or more major cells 42 having one or more interspersed minor cells 44. For example, each of the major cells 42 can extend between a central connecting portion 46 and the radial support member 22. Additionally, each of the minor cells 44 can be disposed between two major cells 42 and be connected at a common junction 48 with the radial support member 22. The expandable frame member 20 is movable between a non-deployed configuration (FIG. 8C) and a deployed configuration (FIG. 8D). The diamond-shaped cells 38 comprising the expandable frame member 20 allow the embolic filter device 10 to be easily collapsed and advanced through the vasculature, while also providing a radial force sufficient to expand the expandable frame member into contact with a blood vessel wall.

Figure 9A:
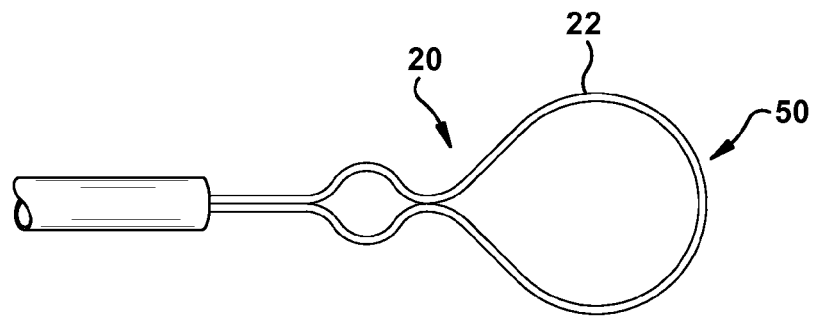
FIGS. 9A-D are perspective views showing another alternative configuration of an expandable frame member comprising the embolic filter device in FIGS. 1A-B.
Figure 9B:
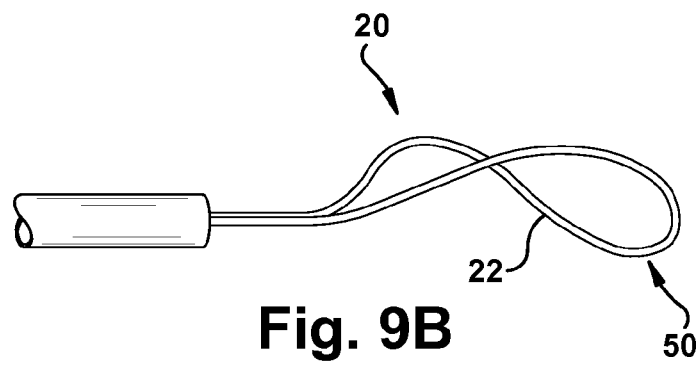
Figure 9C:
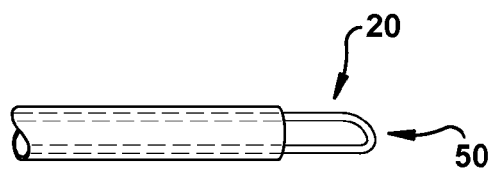
Figure 9D:
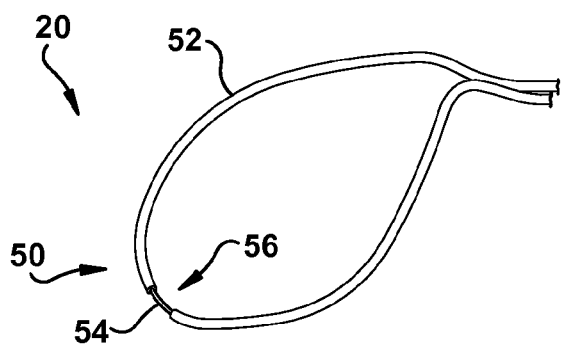

It will be appreciated that the expandable frame member 20 can include additional features to facilitate positioning of the embolic filter device 10 within a blood vessel. For example, the expandable frame member 20 can include at least one bending region 50 (FIGS. 9A-D) configured to facilitate collapse of the expandable frame member into a delivery catheter. Advantageously, a bending region 50 can: (1) reduce or eliminate stress points in the expandable frame member 20; and (2) allow for apposition of the expandable frame member against different diameter blood vessels (e.g., an aorta). In some instances, where the radial support member 22 is comprised of a single filament or wire, a bending region 50 can comprise a portion of the radial support member having a tensile strength that is less than the tensile strength of the regions immediately adjacent the bending region. Alternatively, a bending region 50 can have a different configuration where the expandable frame member 20 has a multi-part structure. For example, the expandable frame member 20 can comprise a metal (e.g., Nitinol or stainless steel) or plastic (e.g., nylon) hypotube 52 (FIG. 9D) having a flexible filament 54 (e.g., a Nitinol or stainless steel wire) disposed therein. In this configuration, the hypotube 52 can include a discontinuous region 56 bridged by the flexible filament 54, Since only the flexible filament 54 spans the discontinuous region 56 (e.g., as opposed to both the hypotube 52 and the filament), the resultant bending region 50 can impart the expandable frame member 20 with increased flexibility at the bending region.

Figure 10A:
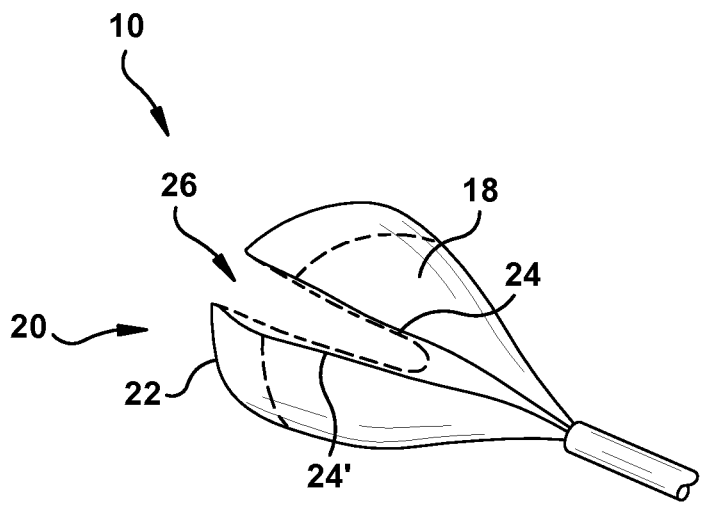
FIG. 10A is a perspective view showing an alternative configuration of the embolic filter device in FIGS. 1A-B.
Figure 10B:
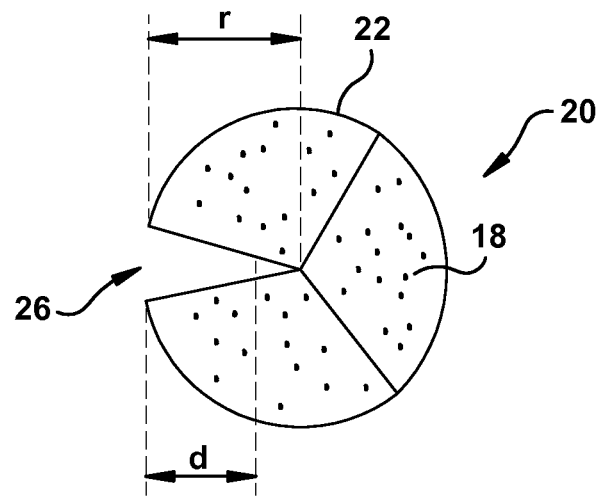
FIG. 10B is a front view of the embolic filter device in FIG. 10A.
Figure 10C:
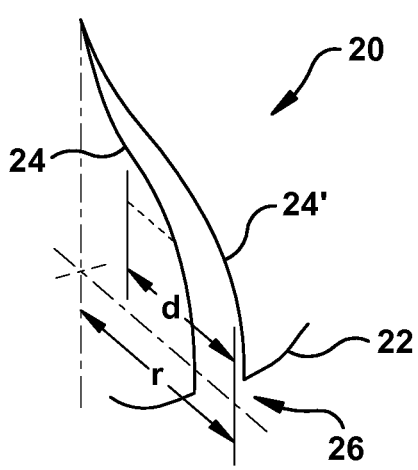
FIG. 10C is a partial cutaway view of the embolic filter device in FIGS. 10A-B.

In another aspect, the embolic filter device 10 can be configured as shown in FIGS. 10A-C. For example, the embolic filter device 10 can comprise an expandable frame member 20 including a radial support member 22 operably connected to oppositely disposed first and second longitudinal struts 24 and 24'. The first and second longitudinal struts 24 and 24' can define an engaging portion 26 shaped and configured to sealingly mate with a portion of an endovascular catheter 28. The embolic filter device 10 can further include a membrane 18 securely connected to the expandable frame member 20 and defining a collection chamber 16 for captured emboli. In some instances, the engaging portion 26 can be substantially free from the membrane 18. The portion of the engaging portion 26 that is free from the membrane 18 can include an entire radial distance r or only a portion thereof. As shown in FIGS. 10B-C, for example, the portion of the engaging portion 26 that is free from the membrane 18 can include a distance d that is less than the radial distance r.

Figure 11A:
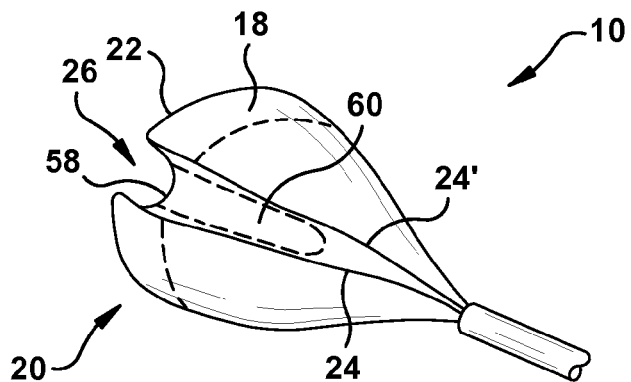
FIG. 11A is a perspective view showing an alternative configuration of the embolic filter device in FIGS. 1A-B.
Figure 11B:
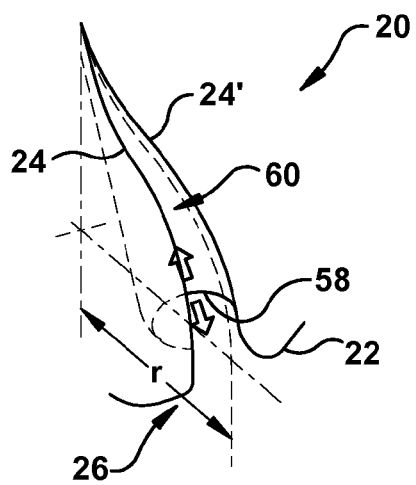
FIG. 11B is a partial cutaway view of the embolic filter device in FIG. 11A.

In another aspect, the engaging portion 26 (FIGS. 11A-C) can comprise a flexible rim 58. In some instances, the flexible rim 58 can have an arcuate shape and a radius of curvature that is equal to, or about equal to, a radius of curvature of a portion of the endovascular catheter 28 with which the flexible rim is temporarily mated. For example, the flexible rim 58 can have a pre-determined radius of curvature (e.g., based on a known radius of curvature of the endovascular catheter 28). Alternatively, the flexible rim 58 can have a radius of curvature that is different than the radius of curvature of the endovascular catheter 28, but can obtain a radius of curvature that his substantially similar to the radius of curvature of a portion of the endovascular catheter with which the flexible rim is temporarily mated. In other instances, the flexible rim 58 can be connected to the radial support member 22 (e.g., disposed between the first and second longitudinal struts 24 and 24') and a portion of the distal peripheral edge 32 of the membrane 18.

The engaging portion 26 can also include an additional membrane component 60, which extends between the flexible rim 58 and the first and second longitudinal struts 24 and 24' to provide the embolic filter device 10 with additional capacity to move and flex. The membrane component 60 can be a continuous part of the membrane 18 itself or, alternatively, a separate piece of material (e.g., identical to the material used to form the membrane) that is attached (e.g., by stitching) to the first and second longitudinal struts 24 and 24' and/or the membrane 18. When the engaging portion 26 comprises the membrane component 60 and/or the flexible rim 58, the engaging portion has a notch-like or cradle-like configuration adapted to sealingly mate with a portion of an endovascular catheter 28.

Figure 11C:
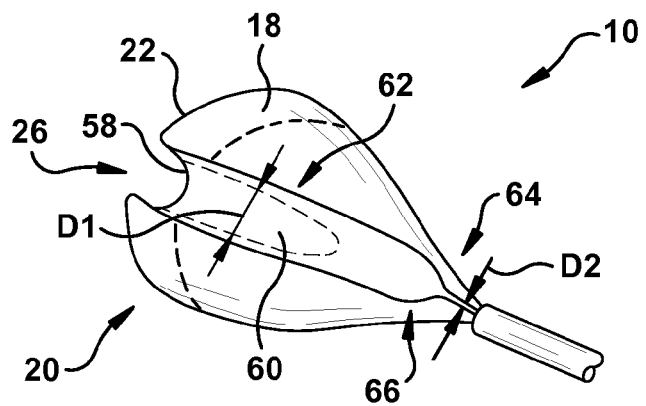
FIG. 11C is a perspective view showing an alternative configuration of the embolic filter device in FIG. 11A.

The flexible rim 58 can be elastic and impart the membrane 18 with an additional degree of rigidity while still allowing the membrane to expand and collapse along with the expandable frame member 20. It will be appreciated that the engaging portion 26 shown in FIGS. 11A-B can alternatively have a bullet-shaped configuration (FIG. 11C). For example, the engaging portion 26 can include a first portion 62 defined by a first distance D1 that extends between the first and second longitudinal struts 24 and 24'. The first distance D1 can be greater than a second distance D2, which extends between the first and second longitudinal struts 24 and 24' adjacent a second portion 64 of the engaging portion 26. A tapered, arcuate junction 66 joins the first and second portions 62 and 64 of the engaging portion 26.

In another aspect, the embolic filter device 10 (FIGS. 12A-C) can include an engaging portion 26 that is similar or identical to the engaging portion shown in FIG. 11C. In some instances, the engaging portion 26 (FIG. 12A) can further comprise a plurality of filamentous members 68 extending between the first and second longitudinal struts 24 and 24'. The filamentous members 68 can extend substantially radial to a longitudinal axis LA of the embolic filter device 10. Alternatively, the filamentous members 68 can extend at an offset angle (e.g., downward or upward) relative to the longitudinal axis LA. Each of the filamentous members 68 can be alternately attached to the first and second longitudinal struts 24 and 24'. The filamentous members 68 can be made of any flexible or semi-rigid material, such as plastic or metal (e.g., Nitinol).

As shown in FIGS. 12B-C, the filamentous members 68 are inwardly deformable. For example, when an endovascular catheter 28 is placed into contact with the engaging portion 26, the filamentous members 68 can deform inward (e.g., towards the longitudinal axis LA), which allows the endovascular catheter to engage a central portion 70 of the expandable frame member 20. As the endovascular catheter 28 is depressed towards the central portion 70, all or only a portion of the filamentous members 68 may spring back to their initial orientation. Return of some or all of the filamentous members 68 to their initial orientation can help to ensure that the endovascular catheter 28 is securely retained within the engaging portion 26 of the embolic filter device 10.

Figure 13A:
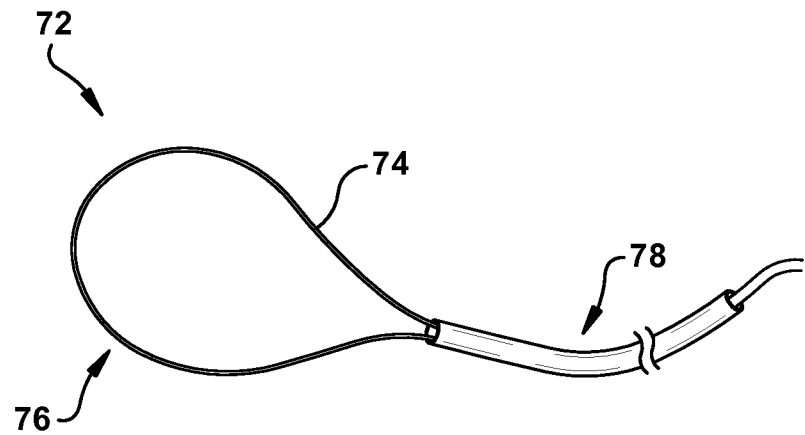
FIG. 13A is a schematic illustration showing a snare mechanism for manipulating the embolic filter device in FIGS. 1A-B.
Figure 13B:
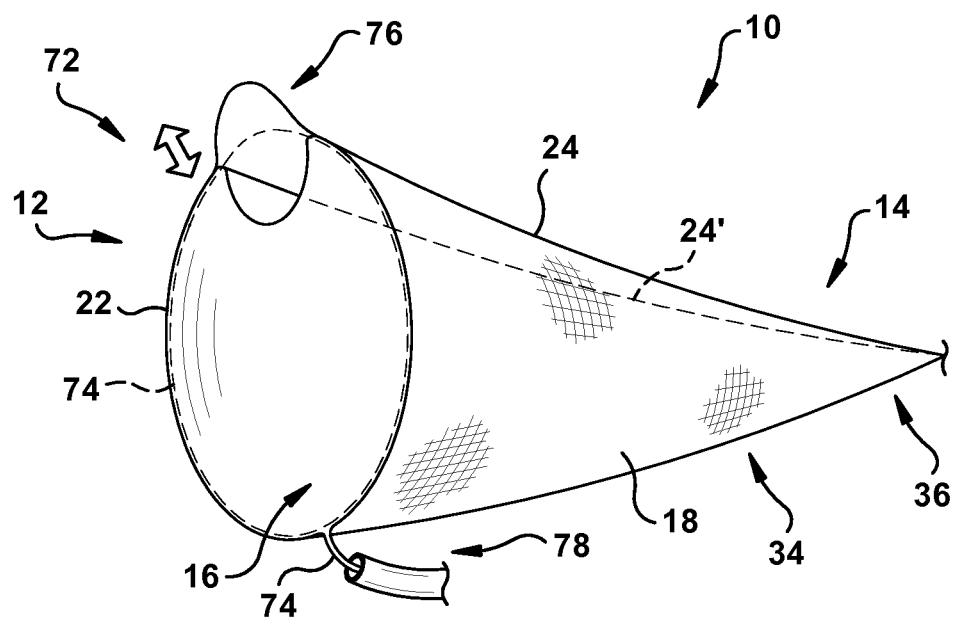
FIG. 13B is a perspective view showing the snare mechanism in FIG. 13A operably connected with an embolic filter device.
Figure 13C:
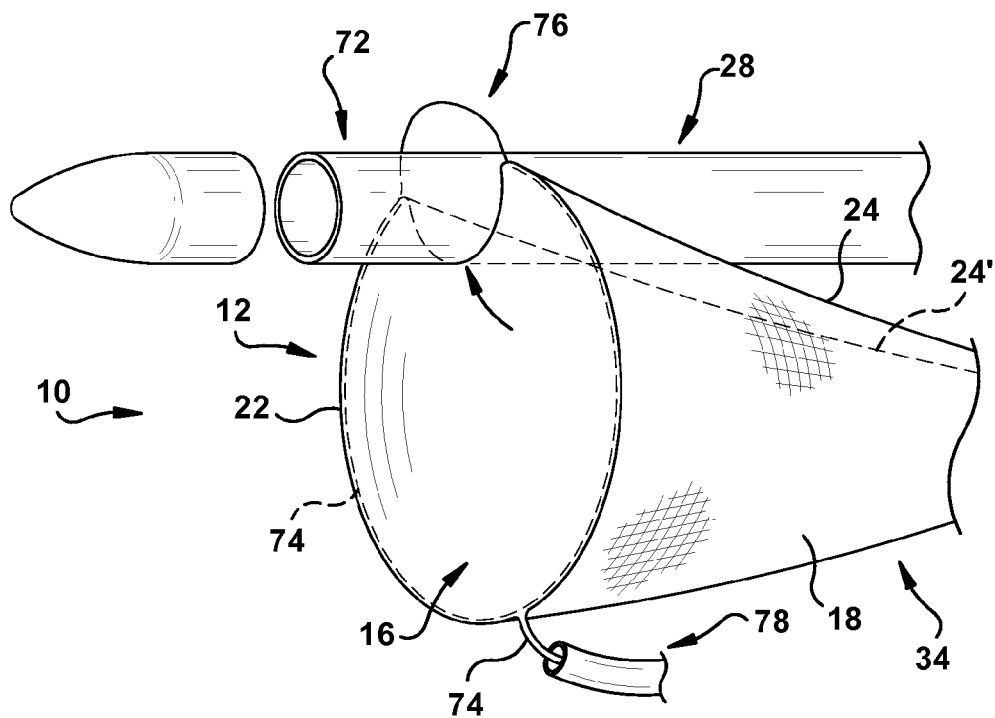
FIG. 13C is a perspective view showing the embolic filter device in FIG. 13B being placed over an endovascular catheter.
Figure 13D:
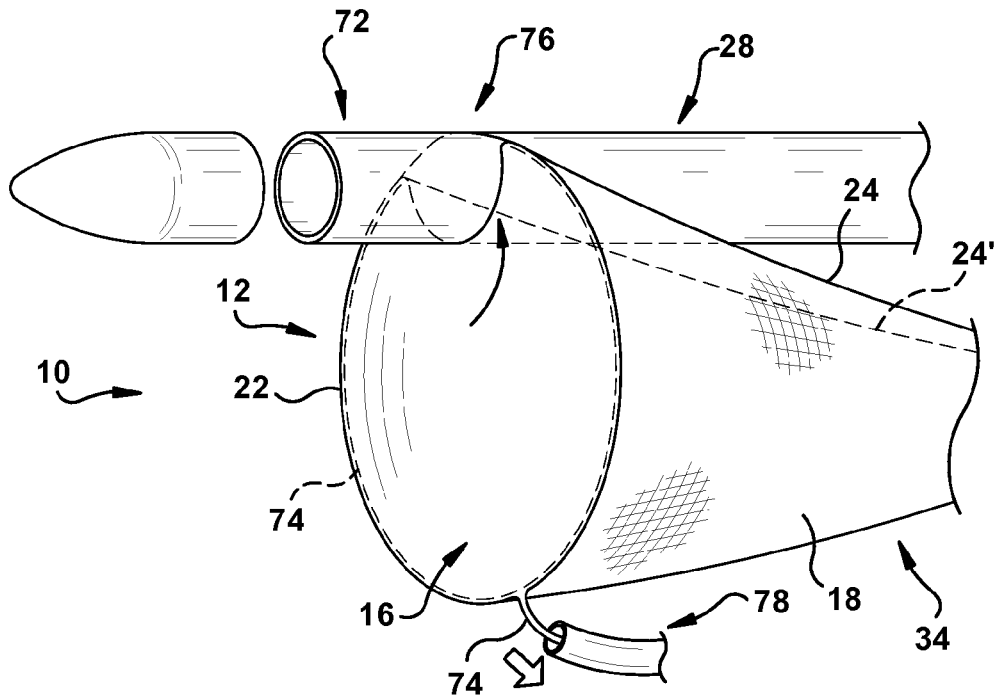
FIG. 13D is a perspective view showing the embolic filter device in FIG. 13C being securely mated with the endovascular catheter using the snare mechanism.

FIGS. 13A-D illustrate another aspect of the present disclosure including a snare mechanism 72 configured for use with the embolic filter device 10. As shown in FIG. 13A, the snare mechanism 72 comprises a continuous filament 74 that is formed at one end into a lasso portion 76, at least a portion of which is adapted to mate with an outer surface of an endovascular catheter 28 (FIGS. 13C-D). The continuous filament 74 (FIG. 13A) can comprise a flexible wire or thread. In some instances, a portion of the continuous filament 74 can be housed within a delivery mechanism 78, such as a catheter. The lasso portion 76 can be selectively enlarged and constricted by advancing or withdrawing the continuous filament 74, respectively, through the delivery mechanism 78.

As shown in FIG. 13B, a portion of the snare mechanism 72 is operably integrated into the embolic filter device 10. More particularly, a portion of the continuous filament 74 can be operably embedded within a portion of the membrane 18 at the proximal peripheral edge 80 thereof. For example, the proximal peripheral edge 80 can be formed into a cuff (not shown) to allow the portion of the continuous filament 74 to be slidably received therein. As shown in FIG. 13B, the portion of the continuous filament 74 can extend about the perimeter of the proximal peripheral edge 80 in a substantially parallel manner with the radial support member 22. With the snare mechanism 72 operably integrated with the embolic filter device 10, the lasso portion 76 is oppositely disposed from the engaging portion 26. As described in more detail below, the snare mechanism 72 can be manipulated to selectively enlarge and contract the lasso portion 76 (indicated by double arrow).

Operation of the snare mechanism 72 with the embolic filter device 10 is illustrated in FIGS. 13C-D. To secure the embolic filter device 10 about an endovascular catheter 28, the continuous filament 74 can first be manipulated to enlarge the lasso portion 76. The lasso portion 76 is enlarged to a diameter sufficient to thread the endovascular catheter 28 therethrough. As shown in FIG. 13C, for example, the lasso portion 76 is placed over the endovascular catheter 28 and then advanced to a desired location about the endovascular catheter.

Once the embolic filter device 10 is properly positioned about the endovascular catheter 28, the continuous filament 74 can be manipulated (e.g., withdrawn, as indicated by arrow) to secure the embolic filter device thereto. More particularly, withdrawal of the continuous filament 74 causes the lasso portion 76 to cinch about the outer surface of the endovascular catheter 28 and thereby mate the engaging portion 26 with the endovascular catheter. The lasso portion 76 can be cinched until the engaging portion 26 sealingly mates with the endovascular catheter 28. Following a medical procedure, the continuous filament 74 can again be manipulated to enlarge the lasso portion 76 and thereby allow the embolic filter device 10 to be slidably removed from over the endovascular catheter 28.

Figure 15A:
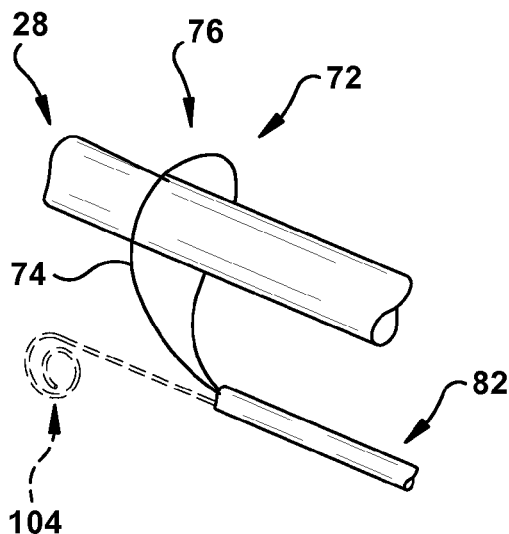
FIG. 15A is a perspective view showing an alternative configuration of the snare mechanism in FIGS. 13A-D being placed over an endovascular catheter.
Figure 15B:
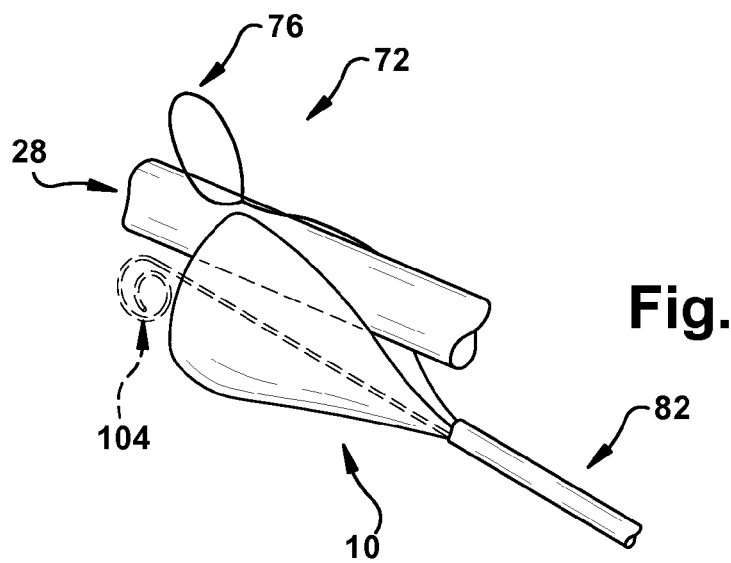
FIG. 15B is a perspective view showing the snare mechanism in FIG. 15A being cinched about the endovascular catheter.
Figure 15C:
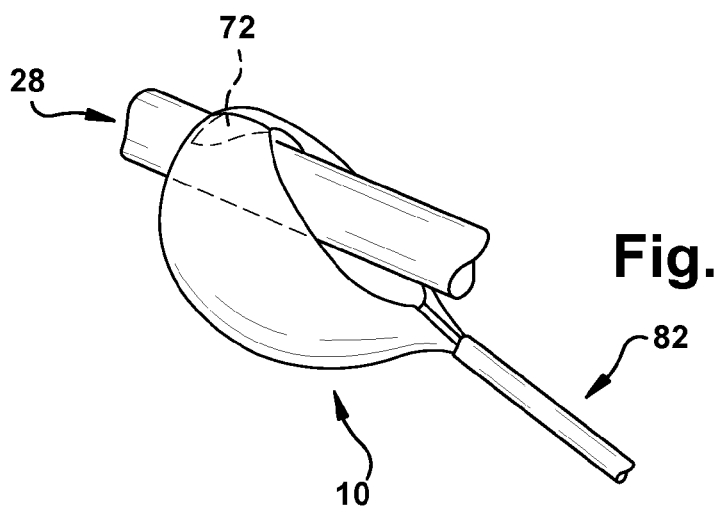
FIG. 15C is a perspective view showing an embolic filter device mated with the endovascular catheter in FIG. 15B.

Another configuration of the snare mechanism 72 is illustrated in FIGS. 15A-C. In some instances, the lasso portion 76 can comprise a continuous filament 74 that is operably connected with the expandable frame member 20. For example, the lasso portion 76 can be operably disposed within the expandable frame member 20 (e.g., where the expandable frame member comprises a hypotube 52). In other instances, a portion of the continuous filament 74 can be housed within a delivery mechanism (not shown), such as a delivery catheter. In this instance, the lasso portion 76 can be selectively enlarged and constricted by advancing or withdrawing the continuous filament 74, respectively, through the delivery mechanism.

In operation, the continuous filament 74 can first be manipulated to enlarge the lasso portion 76 as shown in FIG. 15A. Upon deployment, the lasso portion 76 can expand into contact with substantially all of a blood vessel wall (e.g., an aortic wall). The lasso portion 76 extends away from a multi-lumen delivery catheter 82 at an angle that is greater than 0° relative to the multi-lumen delivery catheter. In one example, the lasso portion 76 can extend at an angle of about 90° relative to the multi-lumen delivery catheter 82. Expansion of the lasso portion 76 ensures that a medical device, such as an endovascular catheter 28 can readily pass therethrough. For instance, after deploying the lasso portion 76 in a blood vessel, an endovascular catheter 28 can be passed through the lasso portion and advanced to a desired anatomical location.

Once the lasso portion 76 is properly positioned about the endovascular catheter 28, the continuous filament 74 can be manipulated (e.g., withdrawn) to secure the embolic filter device 10 thereto. More particularly, withdrawal of the continuous filament 74 causes the lasso portion 76 to twist and cinch about the outer surface of the endovascular catheter 28 and thereby mate the engaging portion 26 with the endovascular catheter (FIG. 15B). The lasso portion 76 can then be cinched until the engaging portion 26 sealingly mates with the endovascular catheter 28 (FIG. 15C). Following a medical procedure, the continuous filament 74 can again be manipulated to untwist and enlarge the lasso portion 76 and thereby allow the embolic filter device 10 to be slidably removed from over the endovascular catheter 28. It will be appreciated that the snare mechanism 72 can be configured for use with any of the embolic filter devices 10 described herein.

Although not shown, it will be appreciated that the embolic filter device can include a dual-function snare mechanism configured to not only capture the endovascular catheter 28 and mate the engaging portion 26 with a portion of the endovascular catheter, but also progressively close the mouth of the collection chamber 16 following removal of the endovascular catheter from the embolic filter device 10 but prior to retrieving/collapsing the embolic filter device back into the multi-lumen delivery catheter 82.

Figure 14A:
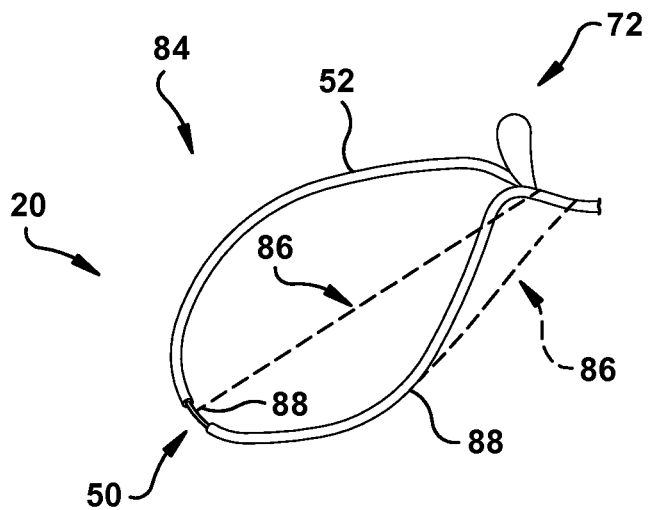
FIG. 14A is a perspective view showing an alternative configuration of the snare mechanism shown in FIGS. 13A-D.

In another aspect, the expandable frame member 20 (such as the one illustrated in FIGS. 9A-D) can include an integral adjustment mechanism 84 (FIGS. 14A-E). The integral adjustment mechanism 84 can include at least one pullwire 86 configured to adapt the membrane 18 to cover substantially all of the cross-sectional area of a blood vessel. As shown in FIG. 14A, the integral adjustment mechanism 84 can include a single pullwire 86 having a distal end 88 that is securely connected to a distal end portion 90 of the expandable frame member 20. The pullwire 86 can further include a proximal end (not shown) that may be manipulated by a user (e.g., a physician) during a medical procedure. The pullwire 86 can be made of any one or combination of materials, such as a metal (e.g., Nitinol or stainless steel) or a polymer (e.g., nylon). It will be appreciated that the integral adjustment mechanism 84 can include more than one pullwire 86, and that the pullwire(s) may be securely connected to other portions of the expandable frame member 20.

Figure 14B:
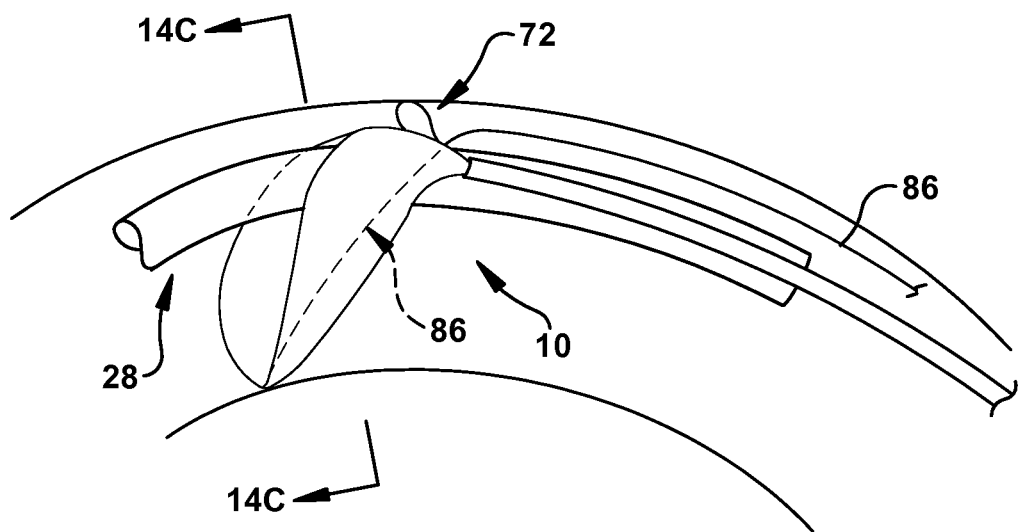
FIG. 14B is a perspective view showing an embolic filter device in FIG. 14A positioned in a blood vessel.
Figure 14C:
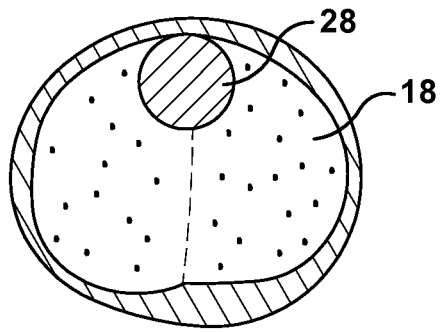
FIG. 14C is a cross-sectional view taken along Line 14C-14C in FIG. 14B.
Figure 14D:
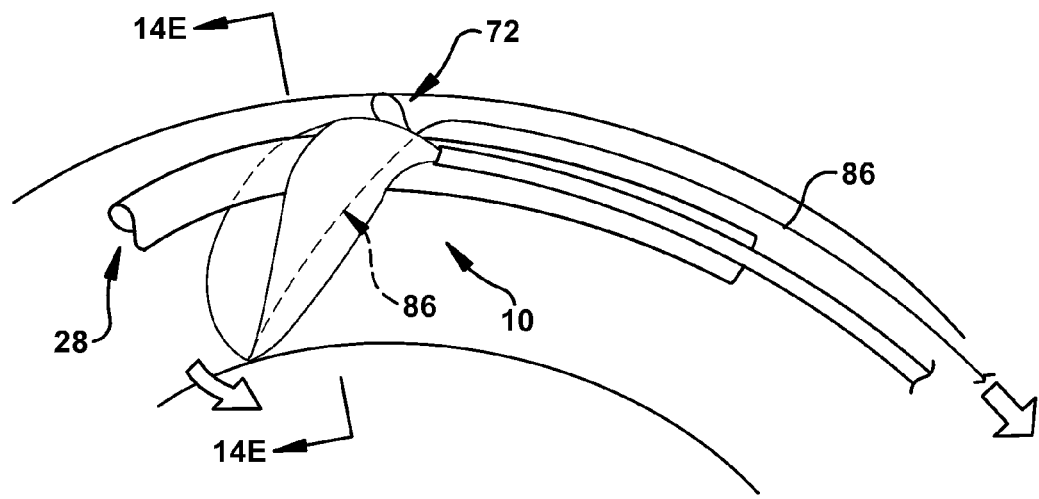
FIG. 14D is a perspective view showing the embolic filter device in FIG. 148 being deployed in the blood vessel.
Figure 14E:
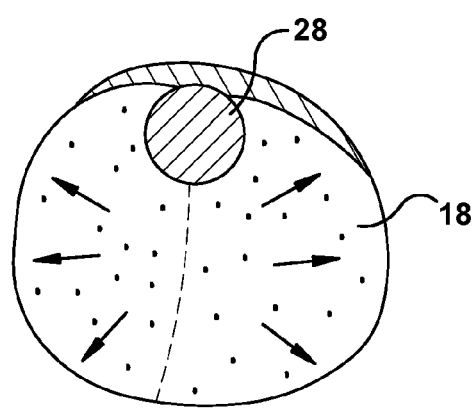
FIG. 14E is a cross-sectional view taken along Line 14E-14E in FIG. 14D.

Operation of the integral adjustment mechanism 84 is illustrated in FIGS. 14B-E. As shown in FIG. 14B, the endovascular catheter 28 is threaded through the lasso portion 76 of the snare mechanism 72 while the embolic filter device 10 is in a non-deployed configuration. In the non-deployed configuration, the membrane 18 of the embolic filter device 10 does not substantially cover the cross-sectional area of the blood vessel (FIG. 14C). Once the embolic filter device 10 and the endovascular catheter 28 are appropriately positioned within the blood vessel, the pullwire 86 can be retracted (indicated by arrow) (FIG. 14D). Retracting the pullwire 86 converts linear translational force to radial force, which causes the expandable frame member 20 to adapt (indicated by arrow) (FIG. 14E) and contact the blood vessel wall so that the membrane 18 substantially covers the cross-sectional area of the blood vessel. For example, actuating the pullwire 86 generates a radial force on the radial support member 22, which causes the diameter of the radial support member to obtain a length that is about equal to the diameter of the blood vessel.

Figure 16A:
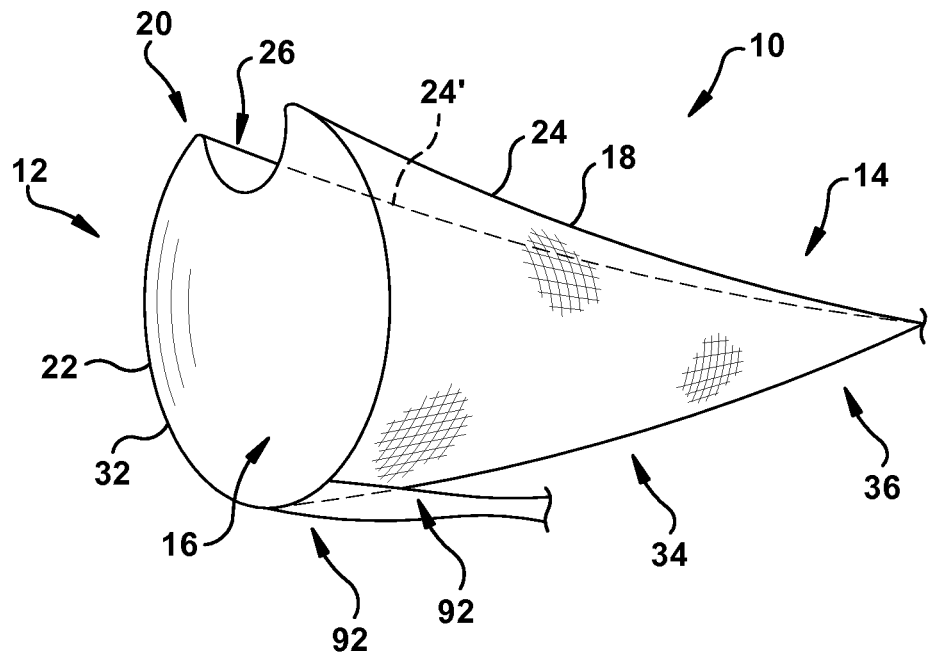
FIG. 16A is a perspective view of an embolic filter device constructed in accordance with another aspect of the present disclosure.
Figure 16B:
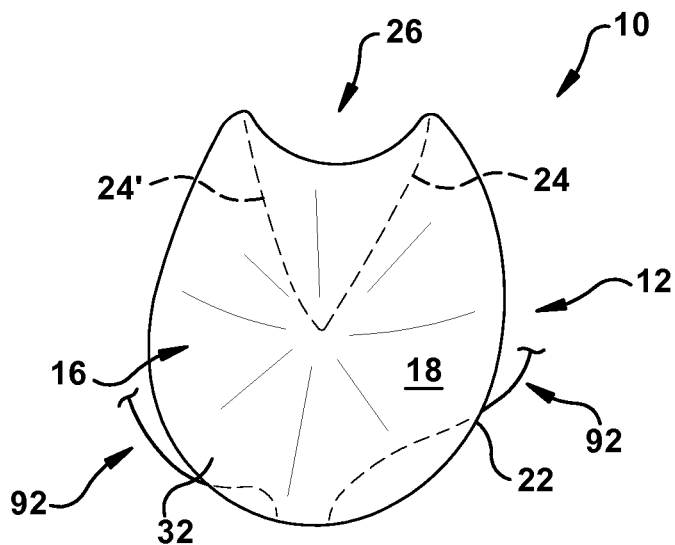
FIG. 16B is a front view of the embolic filter device in FIG. 16A.

It will be appreciated that the embolic filter device 10 can include additional features to facilitate positioning of the embolic filter device within a blood vessel. As shown in FIGS. 16A-B, for example, the embolic filter device 10 can include at least one elongate positioning member 92 configured to provide a counterbalancing force and help orient the embolic filter device within a blood vessel. The at least one elongate positioning member 92 can have a filamentous or wire-like configuration and be made of a flexibly resilient material, such as Nitinol, stainless steel, or a suture material. The at least one elongate positioning member 92 can be oppositely disposed from the longitudinal struts 24 and 24' and connected to the radial support member 22. Where two or more elongate positioning members 92 are included as part of the embolic filter device 10, a distal end of each of the elongate positioning members can be connected to the radial support member 22 at a common point or, alternatively, a distal end of each of the elongate positioning members can be connected to the radial support member at respectively spaced locations on the radial support member. Although not shown in FIGS. 16A-B, it will be appreciated that the embolic filter device 10, and in particular the distal end 36 of the membrane 18, can additionally or optionally include an opening or exit port that permits an elongate positioning member 92 to extend therethrough.

Figure 17:
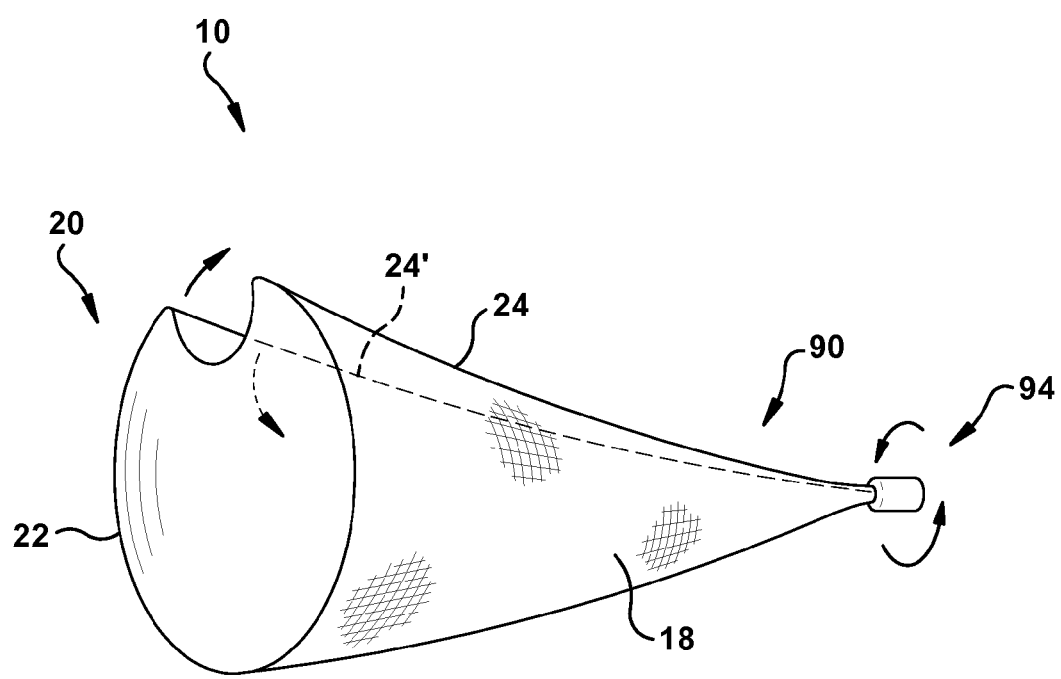
FIG. 17 is a perspective view showing an alternative configuration of the embolic filter device in FIGS. 1A-B.

In another aspect, the expandable frame member 20 can include at least one rotatable collar 94 (FIG. 17). The rotatable collar 94 can be operably fixed to the distal end portion 90 of the expandable frame member 20. The rotatable collar 94 can include one or more bearings (not shown) that allow the expandable frame member 20 to be selectively rotated by manipulating the rotatable collar. For example, the rotatable collar 94 can be manually manipulated to adjust alignment of the engaging portion 26 of the embolic filter device 10 with an endovascular catheter 28. Selective adjustment of the rotatable collar 94 can ensure that the engaging portion 26 snugly contacts the endovascular catheter 28 upon deployment of the embolic filter device 10. The rotatable collar 94 can be made of any one or combination of biocompatible materials, such as stainless steel, Nitinol, or a medical grade plastic.

Systems

Figure 18A:
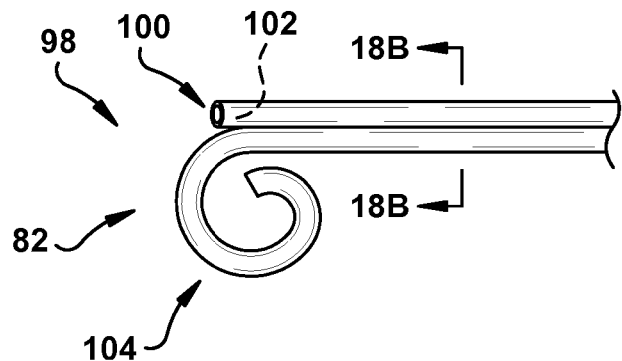
FIG. 18A is a perspective view of a multi-lumen delivery catheter constructed in accordance with another aspect of the present disclosure.
Figure 18B:
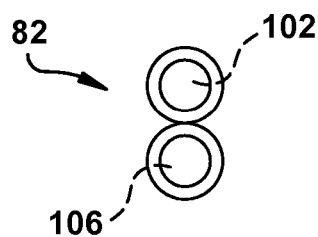
FIG. 18B is a cross-sectional view taken along Line 18B-18B in FIG. 18A.
Figure 18C:
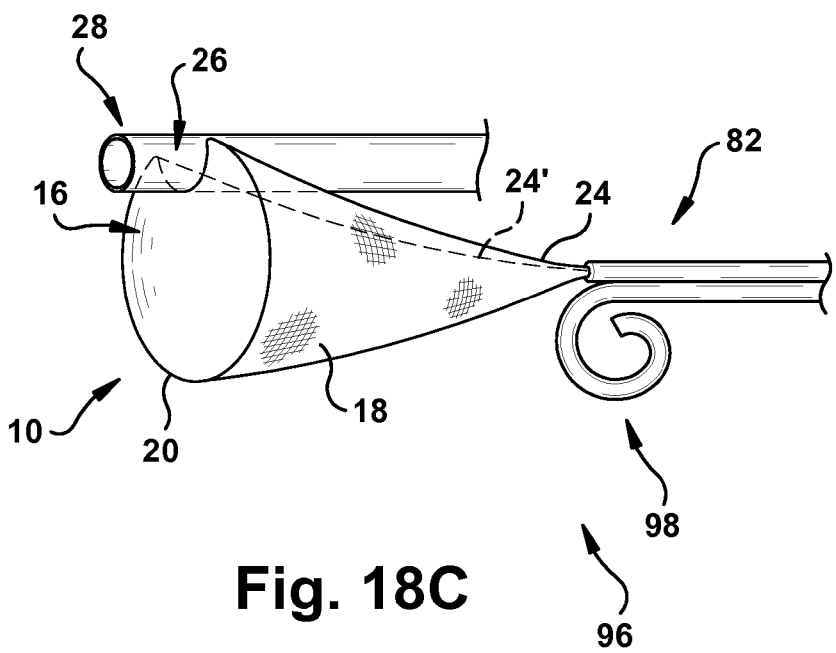
FIG. 18C is a perspective view showing another aspect of the present disclosure comprising an intravascular system for capturing emboli during a medical procedure deployed about an endovascular catheter.

Another aspect of the present disclosure is illustrated in FIGS. 18A-C and includes an intravascular system 96 for capturing emboli during a medical procedure. The system 96 includes an embolic filter device 10 (as described above) and a multi-lumen delivery catheter 82 having a plurality of lumens. The multi-lumen delivery catheter 82 is essentially a pigtail catheter modified to include at least one lumen that is sized, dimensioned, and configured to deploy the embolic filter device 10, and at least one different lumen having a pigtail configuration. As shown in FIG. 18A, the multi-lumen delivery catheter 82 includes a distal end 98 having a first opening 100 for deploying and withdrawing the embolic filter device 10. The multi-lumen delivery catheter 82 further includes a first lumen 102 that is integrally connected with, and extends longitudinally about, a conventional pigtail catheter 104 having a second lumen 106. Advantageously, the multi-lumen delivery catheter 82 enables deployment of both the embolic filter device 10 and radio-opaque contrast without the need for additional surgical access sites.

Figure 19A:
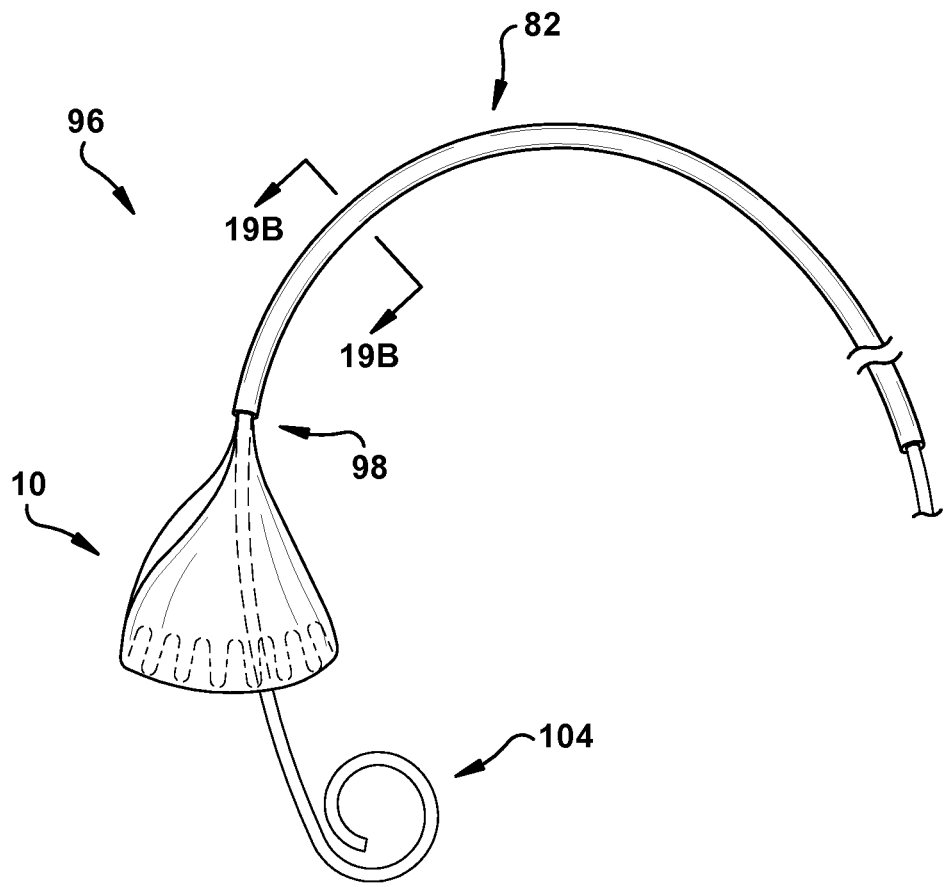
FIG. 19A is a perspective view showing an alternative configuration of the intravascular system in FIGS. 18A-C constructed in accordance with another aspect of the present disclosure.
Figure 19B:
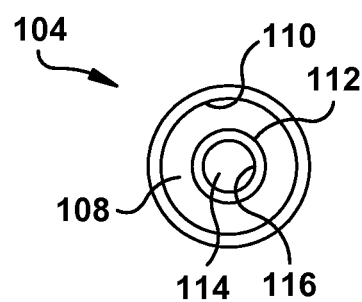
FIG. 19B is a cross-sectional view taken along Line 19B-19B in FIG. 19A.

An alternative configuration of the intravascular system 96 is illustrated in FIGS. 19A-C. The system 96 can include an embolic filter device 10 and a multi-lumen delivery catheter 82. The multi-lumen delivery catheter 82 can comprise an outer lumen 108 defined by a first inner surface 110 and a second outer surface 112. The outer lumen 108 is radially disposed about a central lumen 114, which is defined by a second inner surface 116. The outer lumen 108 can be configured to accommodate the embolic filter device 10. The central lumen 114 can be configured to accommodate a pigtail catheter 104 such that the pigtail catheter can move independently within the central lumen. It will be appreciated that the lumen (not shown in detail) of the pigtail catheter 104 can be configured to accommodate a guidewire (not shown). To permit deployment of the pigtail catheter 104 through the embolic filter device 10, the second end of the membrane 18 can include an opening (not shown) configured to permit movement of the pigtail catheter therethrough.

Methods

Figure 20:
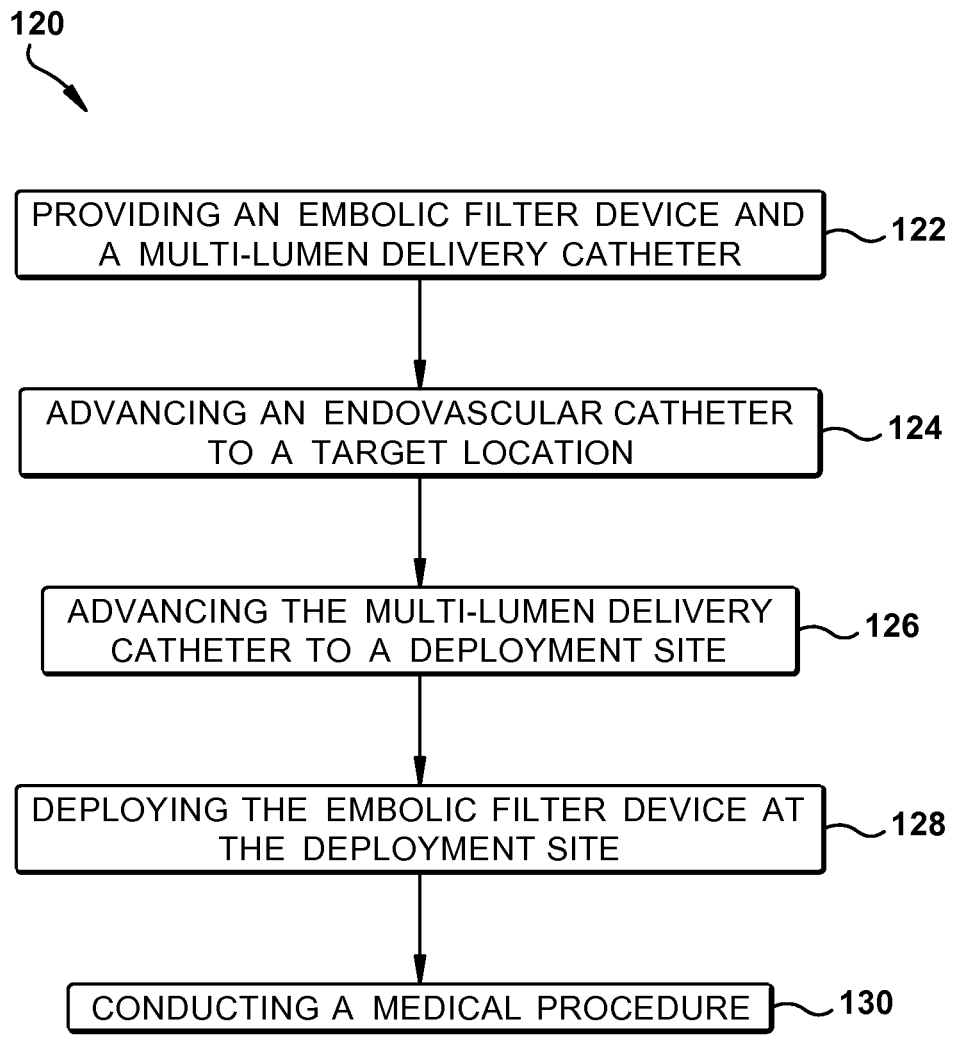
FIG. 20 is a process flow diagram illustrating a method for capturing emboli during a medical procedure according to another aspect of the present disclosure.

Another aspect of the present disclosure is illustrated in FIG. 20 and includes a method 120 for capturing emboli during a medical procedure. The method 120 is described below in terms of capturing emboli during TAVI; however, it should be appreciated that the method can find use in any catheter-based or interventional procedure where there is a potential risk of emboli traveling to downstream organ systems.

One step of the method 120 includes providing an embolic filter device 10 and a multi-lumen delivery catheter 82 (Step 122). The embolic filter device 10 used in the method can be selected based on the type of medical procedure being performed and, in particular, on the size and type of endovascular catheter 28 to be used. In one example, the embolic filter device 10 selected for the method 120 can be identically or similarly constructed as the embolic filter device in FIGS. 1A-B. For example, the embolic filter device 10 can comprise an expandable frame member 20 that is securely connected to a membrane 18, which defines a collection chamber 16 for captured emboli. The frame member 20 can include a radial support member 22 operably connected to at least one longitudinal strut 24. The radial support member 22 can include an engaging portion 26 that is shaped and configured to sealingly mate with a portion of an endovascular catheter 28. The embolic filter device 10 can be pre-loaded in the multi-lumen delivery catheter 82 (e.g., so that the system 96 is ready for use upon removal from a packing). Alternatively, the embolic filter device 10 can be loaded into the multi-lumen delivery catheter 82 by a user prior to use.

Figure 21:
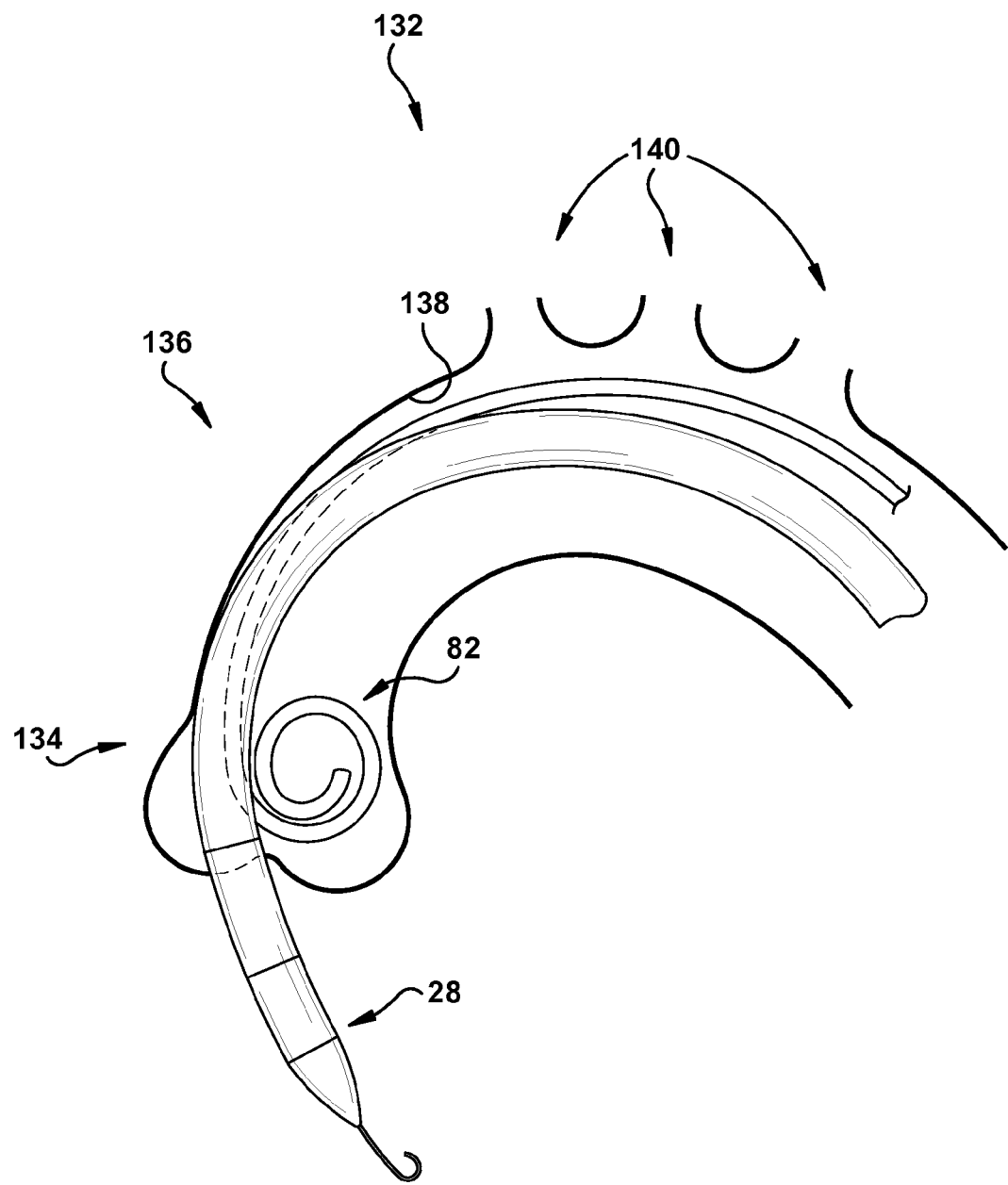
FIG. 21 is a perspective view showing the intravascular system in FIG. 18A being deployed about an endovascular catheter in an ascending aorta.

At Step 124, an endovascular catheter 28 can be advanced to a target location in a subject. As shown in FIG. 21, for example, an endovascular catheter 28 can be advanced across the aortic arch 132 and down through a diseased aortic valve 134. During advancement of the endovascular catheter 28, the multi-lumen delivery catheter 82 is also advanced to a deployment site that is proximate the target location (Step 126). For example, the distal end 118 of the multi-lumen delivery catheter 82 is advanced to a deployment site in the ascending aorta 136 that is proximate the diseased aortic valve 134. Once the distal end 118 of the multi-lumen delivery catheter 82 is appropriately positioned at the deployment site, radio-opaque contrast can be delivered through the second lumen 106 of the pigtail catheter 104 to confirm the position of a prosthetic valve (not shown).

Figure 22:
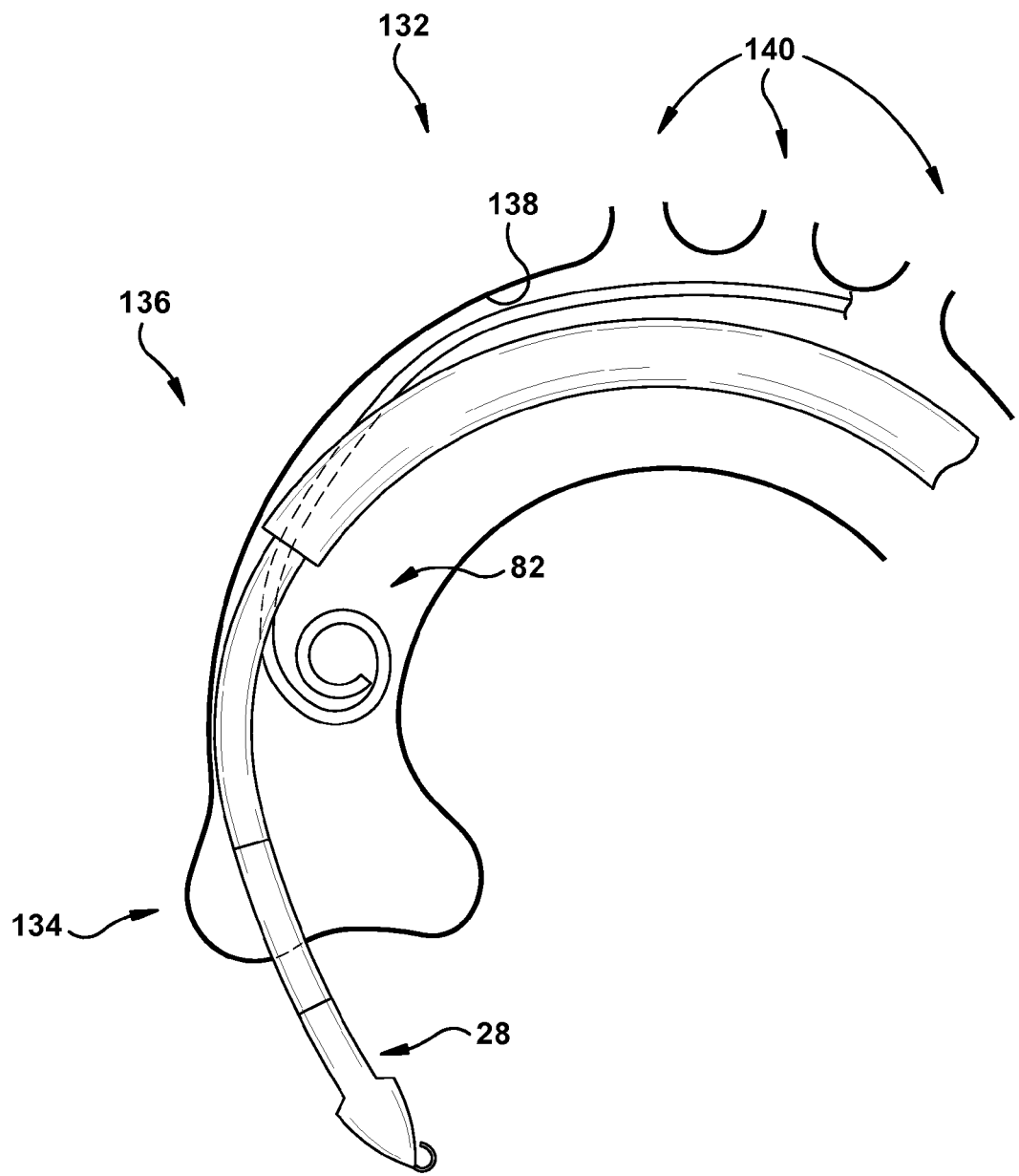
FIG. 22 is a perspective view showing partial deployment of the endovascular catheter in FIG. 21.
Figure 23:
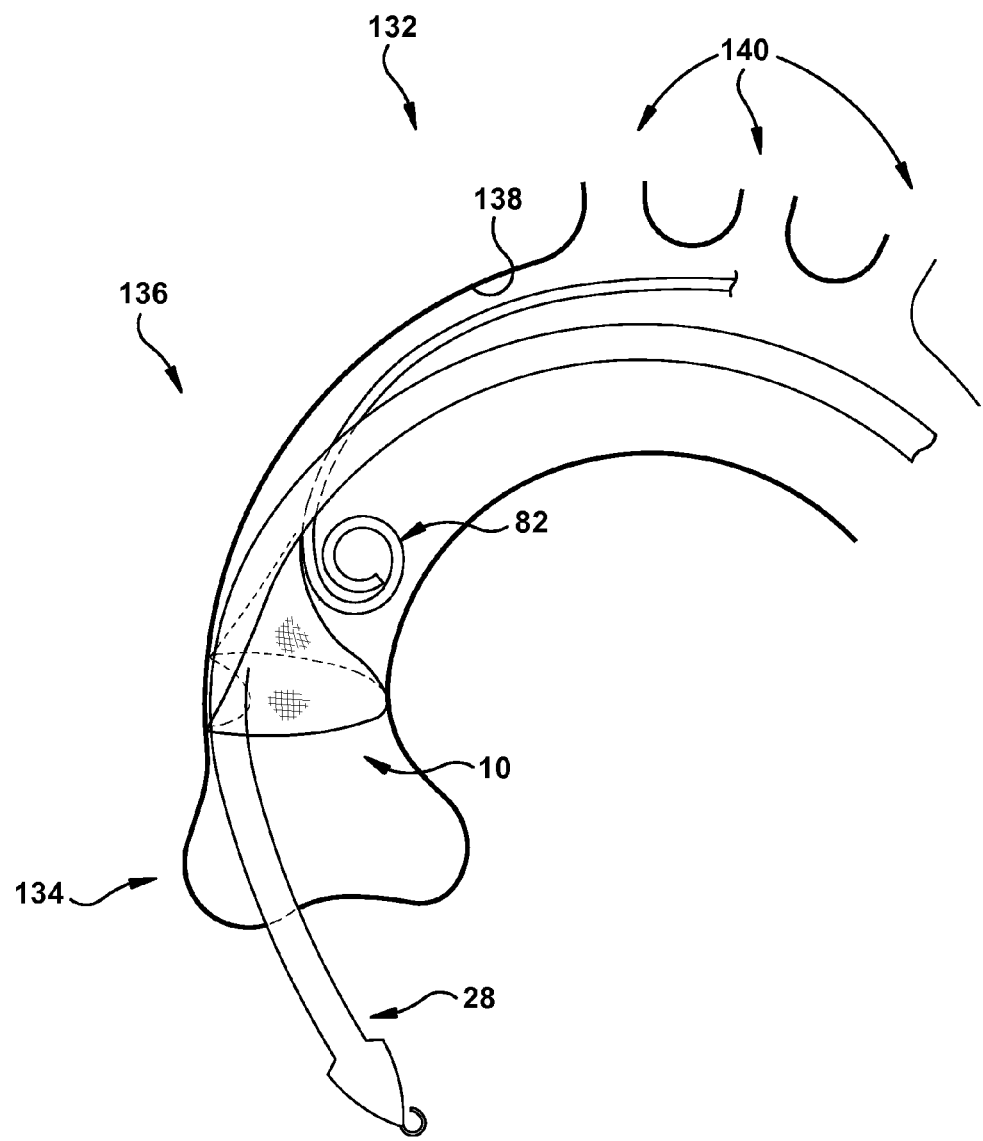
FIG. 23 is a perspective view showing the embolic filter device of FIGS. 1A-B deployed in the ascending aorta.

As shown in FIG. 22, the multi-lumen delivery catheter 82 is then slightly withdrawn prior to deploying the prosthetic valve (or before pacing is started). Next, the embolic filter device 10 is deployed at Step 128. The embolic filter device 10 can be progressively exuded from the first lumen 102 of the multi-lumen delivery catheter 82 using a push rod (not shown) or other similar mechanism capable of advancing the embolic filter device through the first lumen towards the deployment site. As the embolic filter device 10 emerges from the multi-lumen delivery catheter 82, the frame member 20 self-expands into contact with the endovascular catheter 28 and the luminal wall 138 of the ascending aorta 136 (FIG. 23). More particularly, the engaging portion 26 of the radial support member 22 sealingly engages a portion of the outer wall of the endovascular catheter 28, while the remaining portion of the radial support member forms a seal with the luminal wall 138 of the ascending aorta 136.

With the embolic filter device 10 fully deployed at the deployment site, the membrane 18 substantially covers all of the cross-sectional area of the ascending aorta 136 so that the passage of emboli of a certain size is excluded. Additionally, the engaging portion 26 is sealingly mated with the endovascular catheter 28 so that movement of the endovascular catheter will not jostle or dislodge the embolic filter device 10 and thereby risk passage of emboli into downstream organ systems.

At Step 130, the medical procedure is conducted by replacing (or displacing) the diseased aortic valve 134 with the prosthetic valve. During and/or after the procedure, any emboli are captured in the collection chamber 16 of the embolic filter device 10 and thereby prevented from traveling through the aortic arch vessels 140 into the cerebral circulation. Upon completion of the procedure, the embolic filter device 10 can be collapsed into the multi-lumen delivery catheter 82 and withdrawn (along with the endovascular catheter 28) from the subject.

Figure 24:
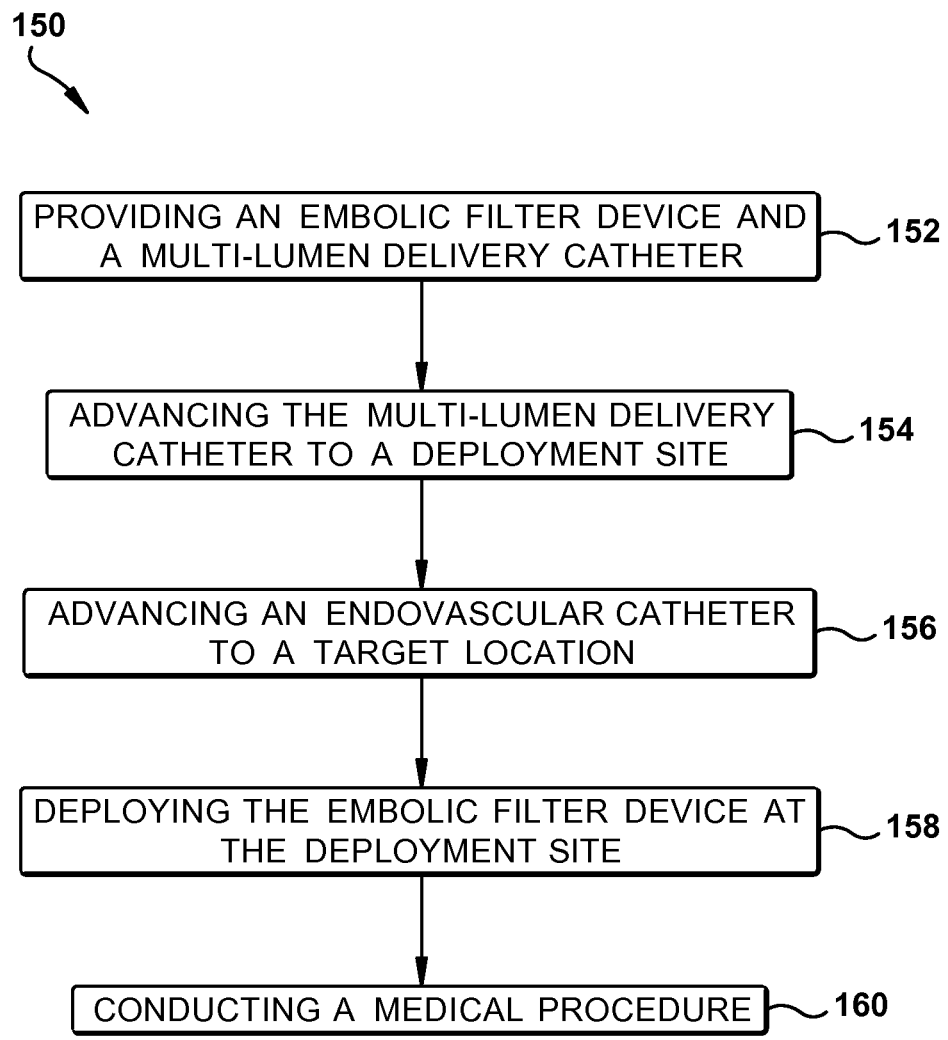
FIG. 24 is a process flow diagram illustrating another method for capturing emboli during a medical procedure according to an aspect of the present disclosure.

Another aspect of the present disclosure is illustrated in FIG. 24 and includes a method 150 for capturing emboli during a medical procedure. One step of the method 150 can include providing an embolic filter device 10 and a multi-lumen delivery catheter 82 (Step 152). The embolic filter device 10 can be pre-loaded in the multi-lumen delivery catheter 82 (e.g., so that the system 96 is ready for use upon removal from a packing). Alternatively, the embolic filter device 10 can be loaded into the multi-lumen delivery catheter 82 by a user prior to use.

Figure 25A:
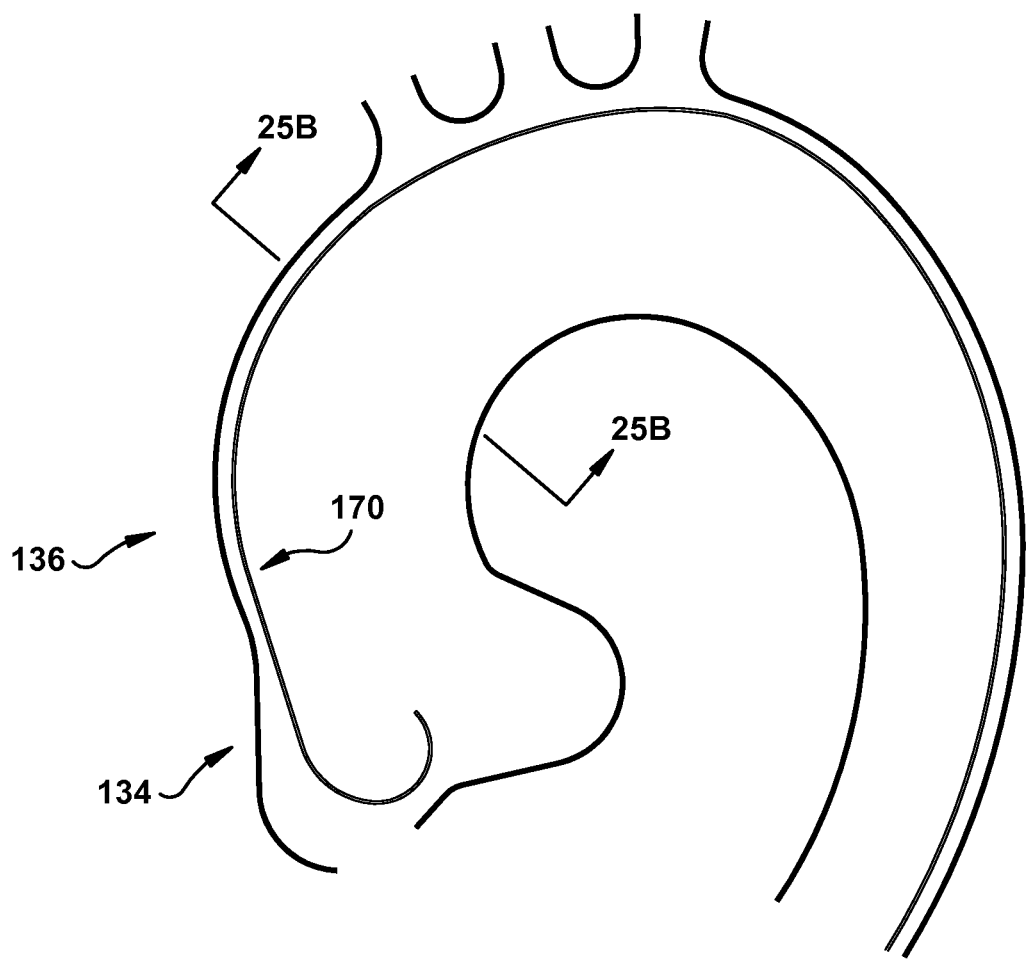
FIGS. 25A-X are a series of schematic illustrations depicting the method in FIG. 24.
Figure 25B:
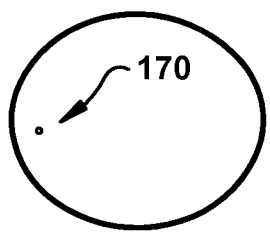
Figure 25C:
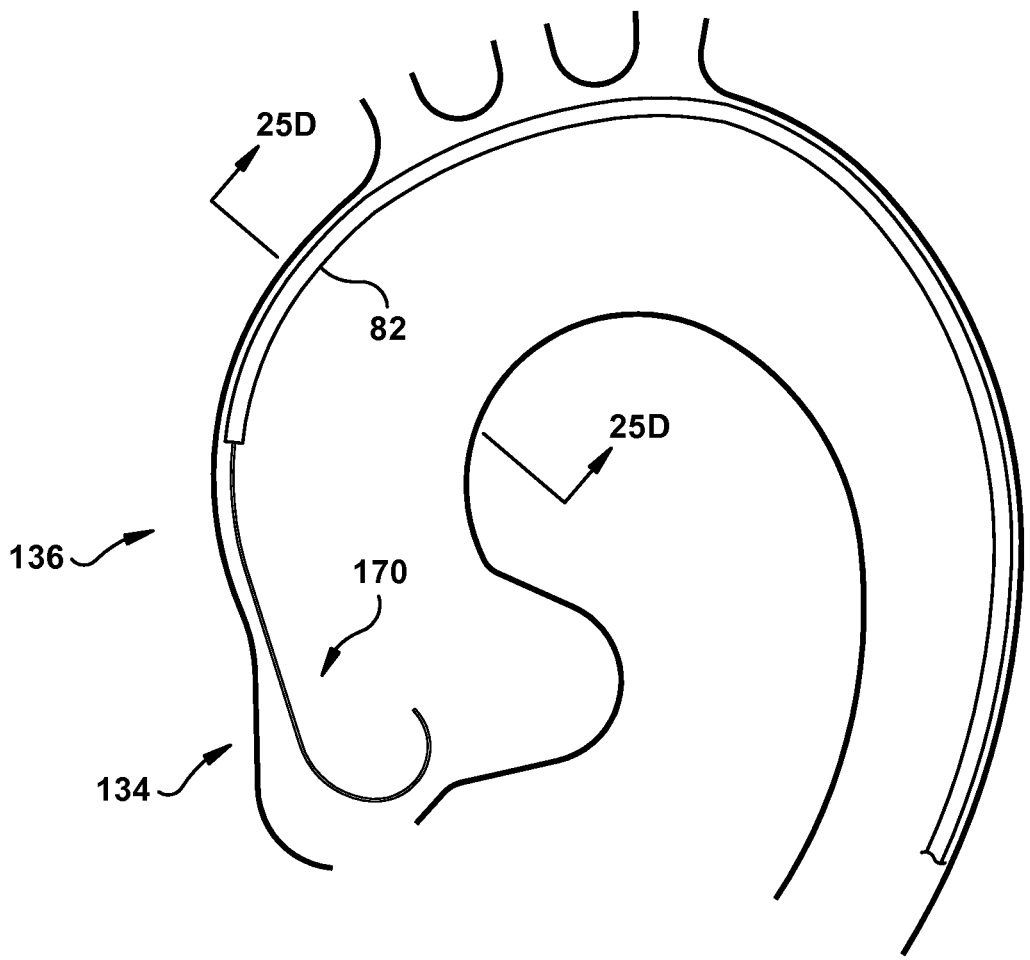
Figure 25D:
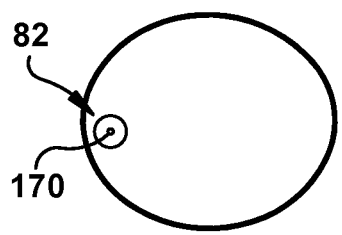

The method 150 can begin by gaining intravascular access at a peripheral venous or arterial site (not shown) of a subject. As shown in FIGS. 25A-B, a first guidewire 170 can then be inserted into the access site and progressively urged through the vasculature of the subject until a distal end of the first guidewire is positioned proximate a diseased aortic valve 134. Once the first guidewire 160 is in place, an embolic filter device 10, such as the device illustrated in FIGS. 11A-C can be loaded into the outer lumen 108 of the multi-lumen delivery catheter 82. As shown in FIGS. 25C-D, the multi-lumen delivery catheter 82 can then be advanced over the first guidewire 170 into the ascending aorta 136 (Step 154). For example, the multi-lumen delivery catheter 82 can be advanced over the first guidewire 170 by threading the first guidewire through the central lumen 114 of the multi-lumen delivery catheter.

Figure 25E:
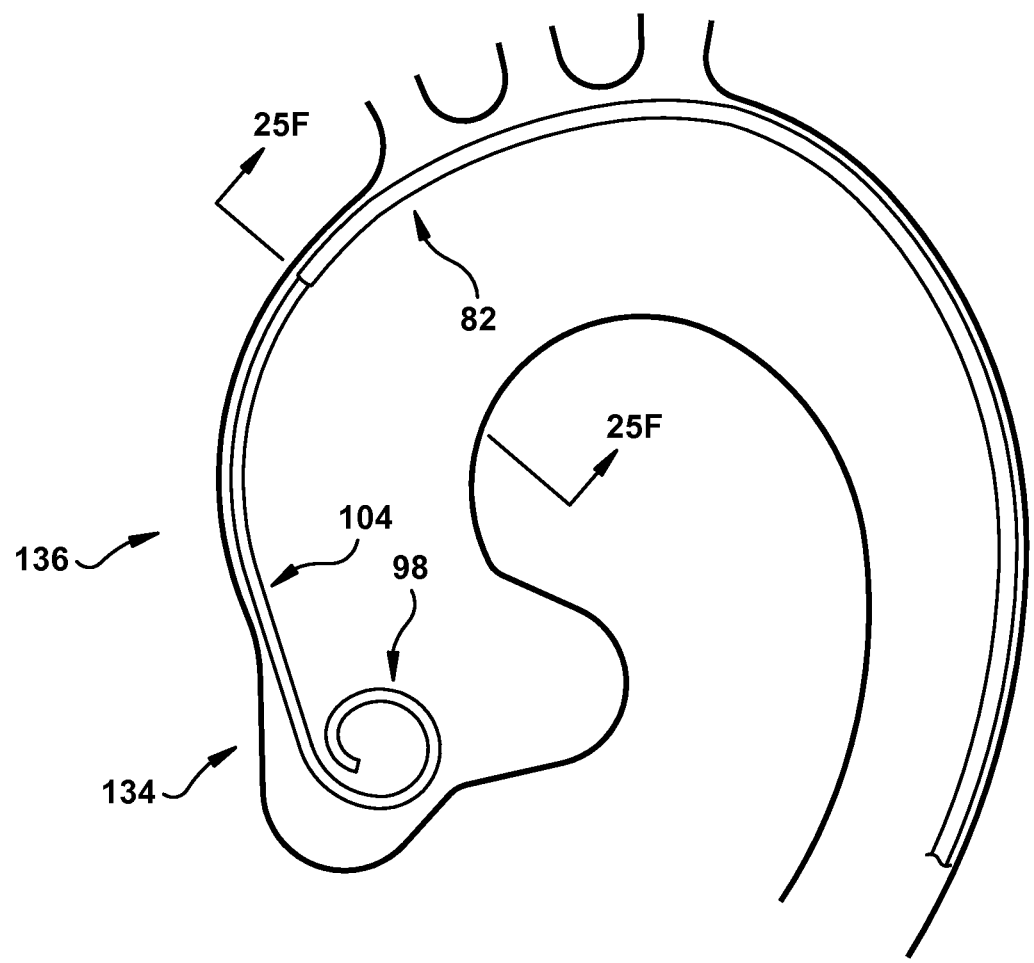
Figure 25F:
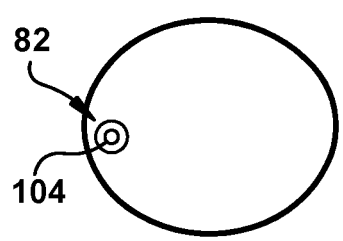

After the multi-lumen delivery catheter 82 is appropriately positioned in the ascending aorta 136, the first guidewire 170 can be withdrawn from the multi-lumen delivery catheter and removed from the subject. A pigtail catheter 104 can then be inserted into the central lumen 114 of the multi-lumen delivery catheter 82. As shown in FIGS. 25E-F, the pigtail catheter 104 can be advanced through the central lumen 114 until a distal end 98 of the pigtail catheter is proximate the diseased aortic valve 134. Contrast can then be infused into the pigtail catheter 104 and dispersed from the distal end 98 thereof to properly image the aortic valve 134 and/or any surrounding anatomical structures. Alternatively, both the pigtail catheter 104 and the device 10 can be loaded together over the first guidewire 170 in the first instance and then the first guidewire removed.

Figure 25G:
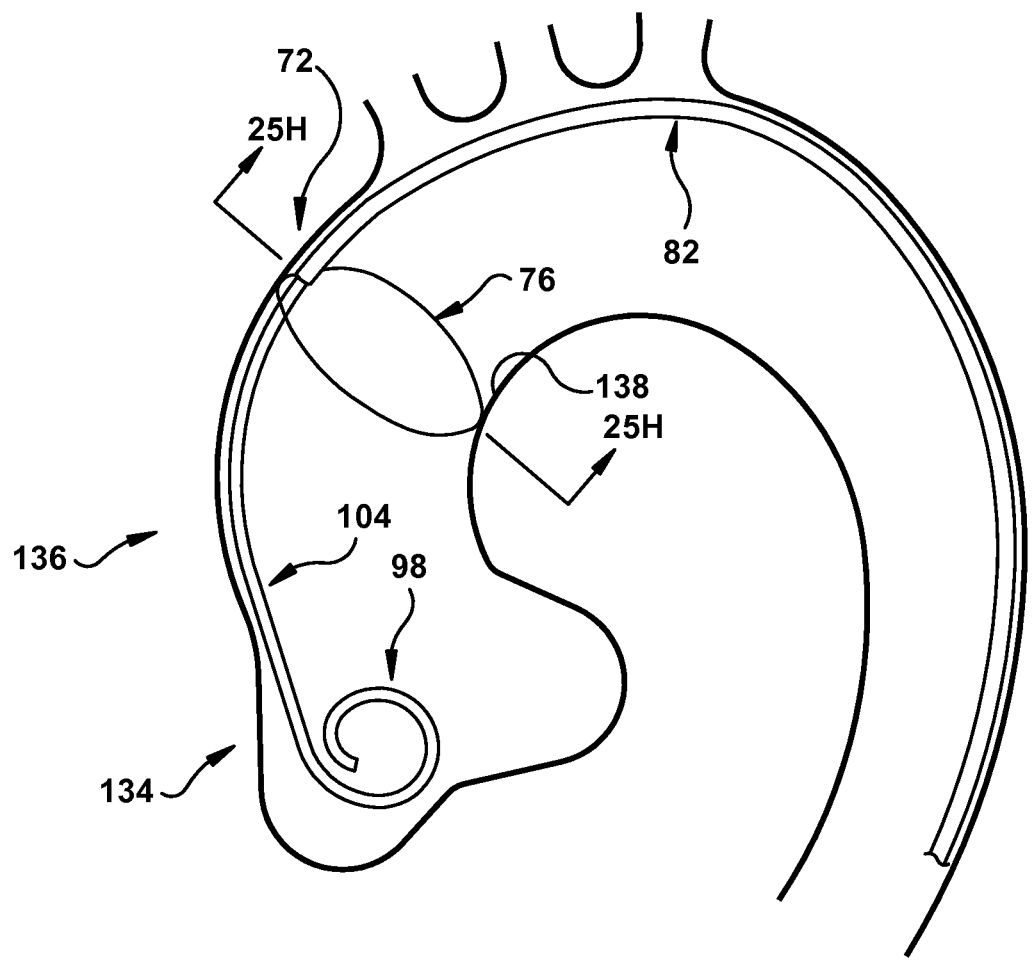
Figure 25H:
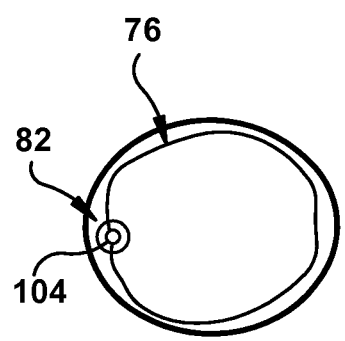
Figure 25I:
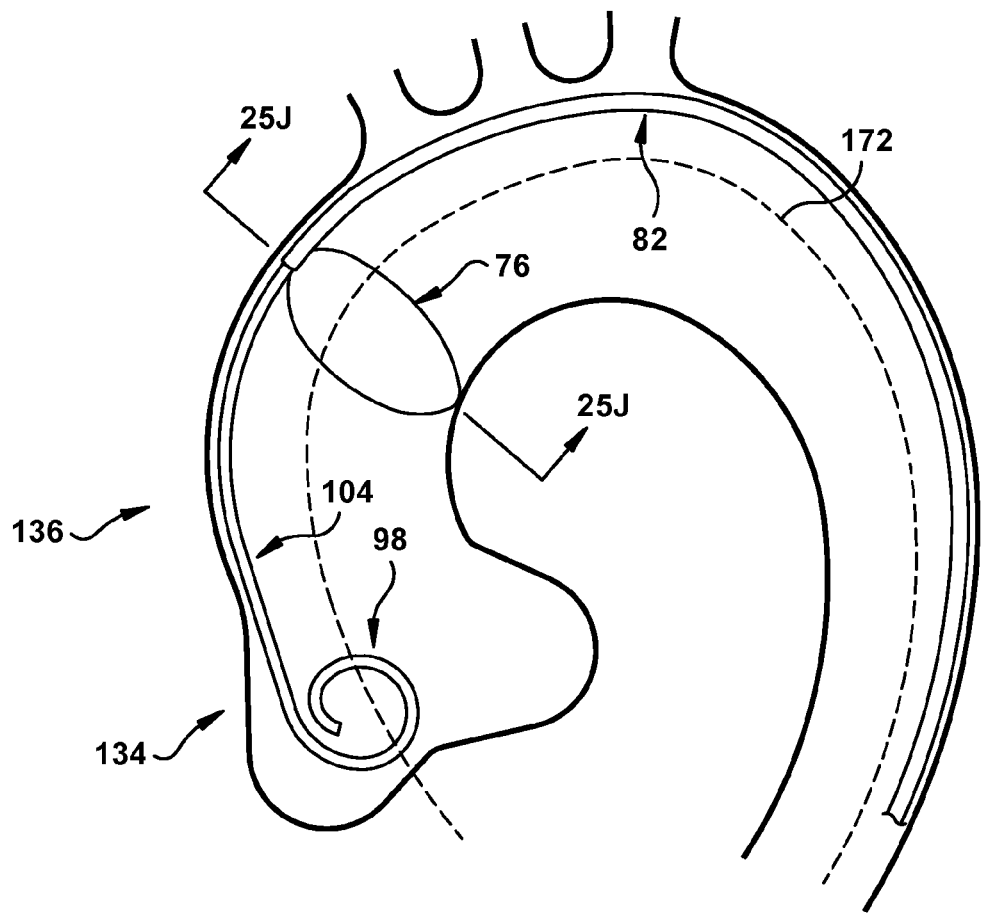
Figure 25J:
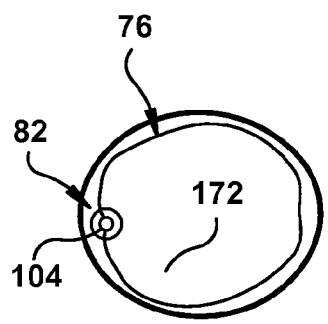

Next, the snare mechanism 72 can be deployed from the multi-lumen delivery 82. As shown in FIGS. 25G-H, for example, deployment of the snare mechanism 72 causes the lasso portion 76 to expand into direct contact with substantially all of the aortic luminal wall 138 such that the lasso portion itself is essentially perpendicular to the direction of aortic blood flow. Once the snare mechanism 72 has been successfully deployed, a second guidewire 172 can be inserted into the vasculature of the subject at a surgical access site that is different than the access site used for the first guidewire 170. The second guidewire 172 can be advanced through the ascending aorta 136 towards the aortic valve 134 such that the second guidewire passes through the lasso portion 76 of the snare mechanism 72 (FIGS. 25I-J).

Figure 25K:
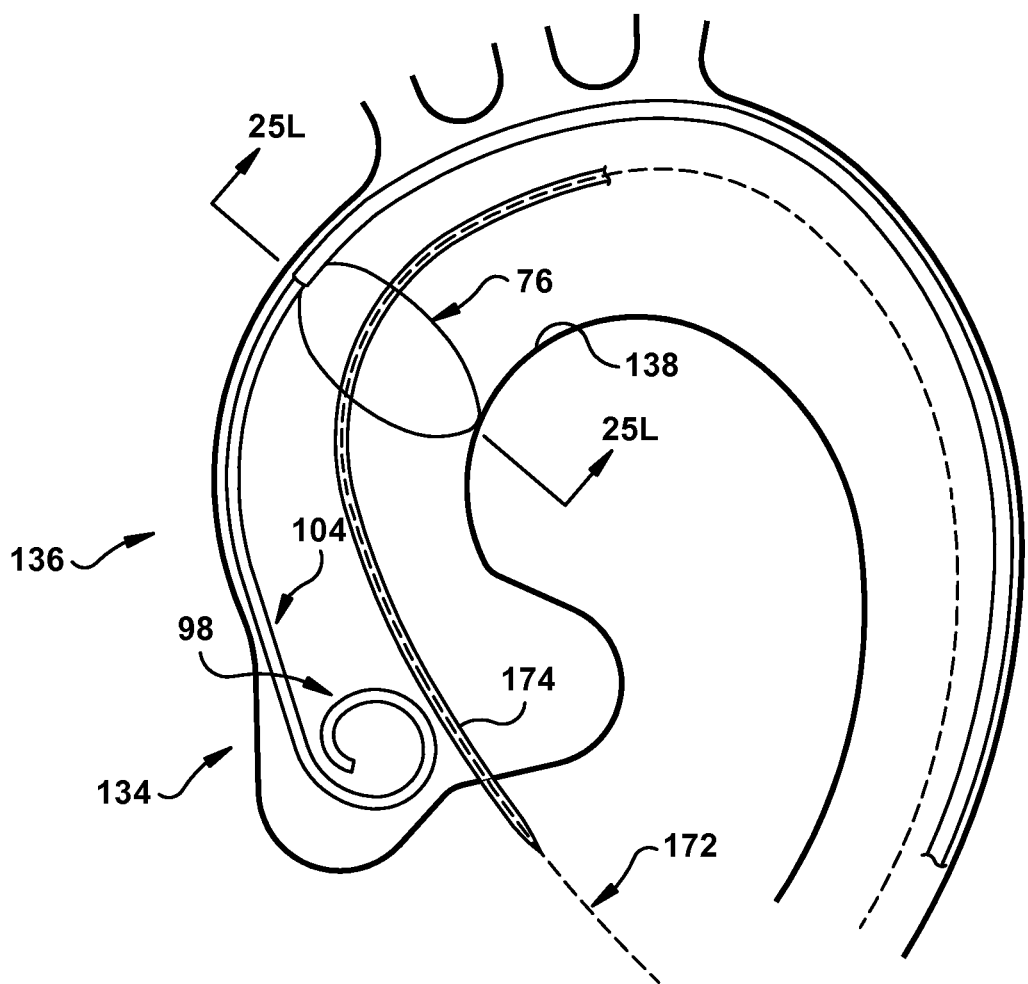
Figure 25L:
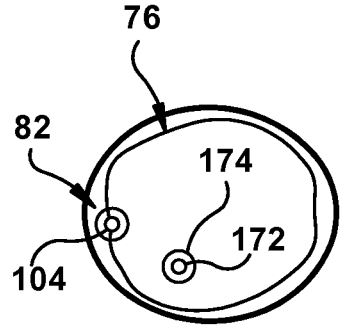
Figure 25M:
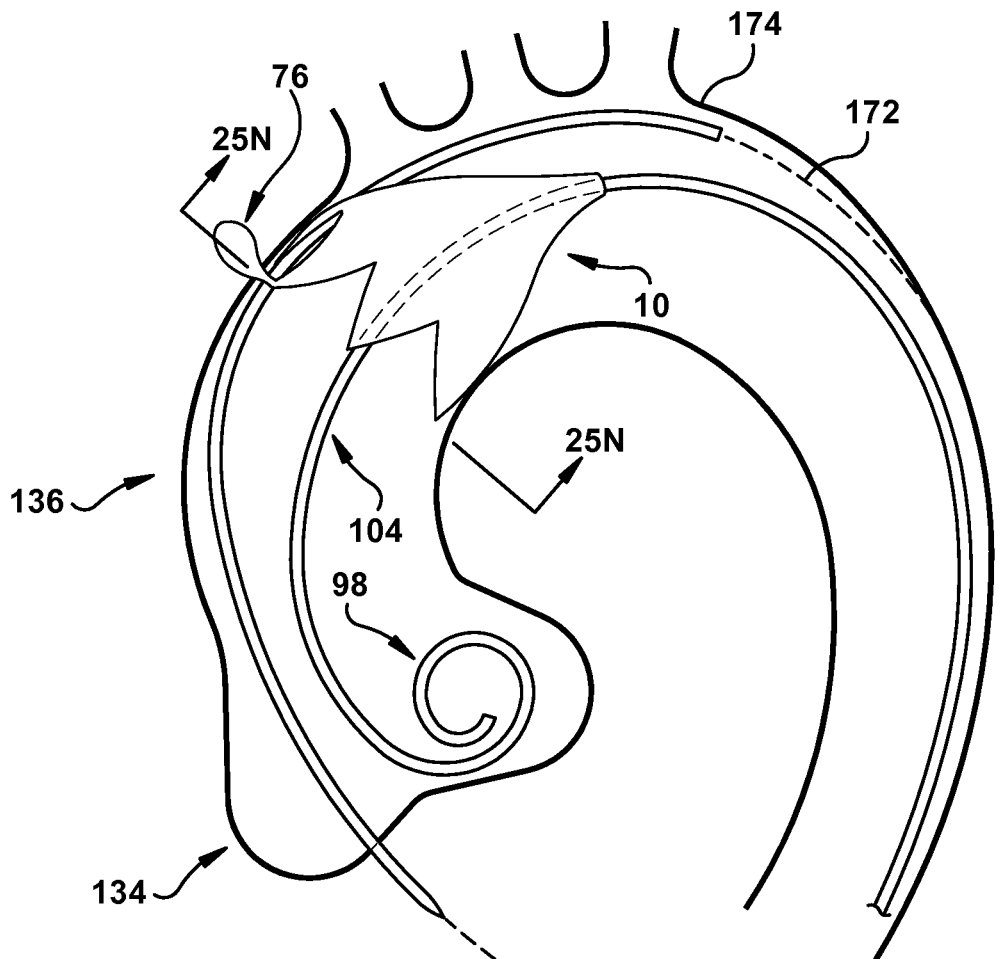
Figure 25N:
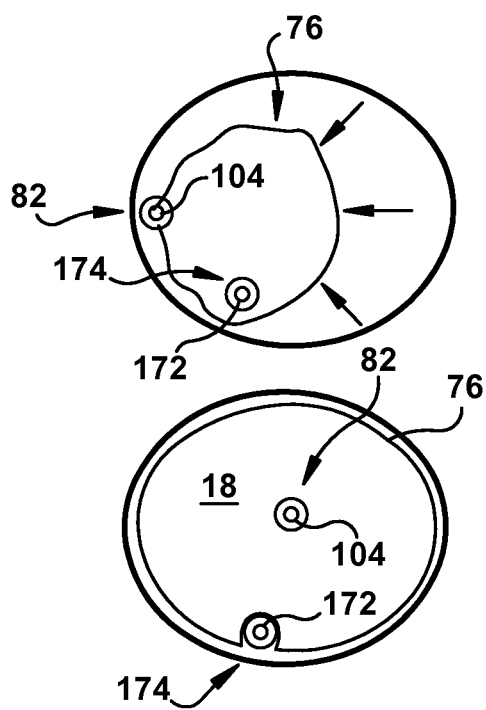

After the second guidewire 172 is appropriately positioned, an endovascular catheter 28, such as a balloon valvuloplasty catheter (BAV) 174 is advanced over the second guidewire as shown in FIGS. 25K-L (Step 156). With the BAV 174 threaded through the lasso portion 76, the snare mechanism 72 is operated (e.g., pulled) so that the lasso portion 76 is cinched about the BAV (indicated by arrows in FIG. 25N), thereby displacing the BAV to the luminal wall 138 of the ascending aorta 136. Next, the multi-lumen delivery catheter 82 is slightly withdrawn to progressively free the embolic filter device 10 therefrom (FIGS. 25M-N) (Step 158). As the embolic filter device 10 is withdrawn, the BAV 174 can be guided into the engaging portion 26. If needed, the snare mechanism 72 can be further operated to assist in positioning the BAV 174 within the engaging portion 26.

Figure 25O:
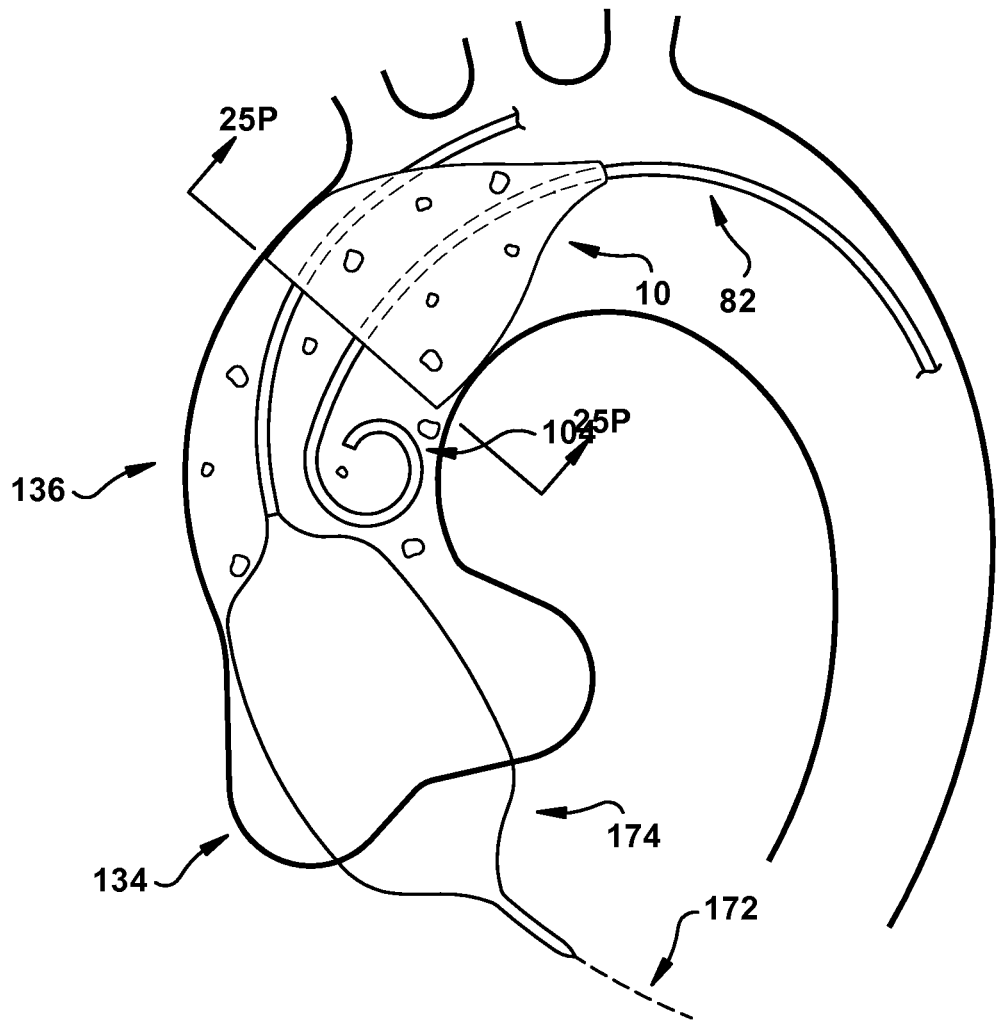
Figure 25P:
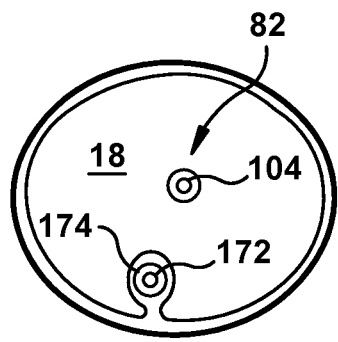
Figure 25Q:
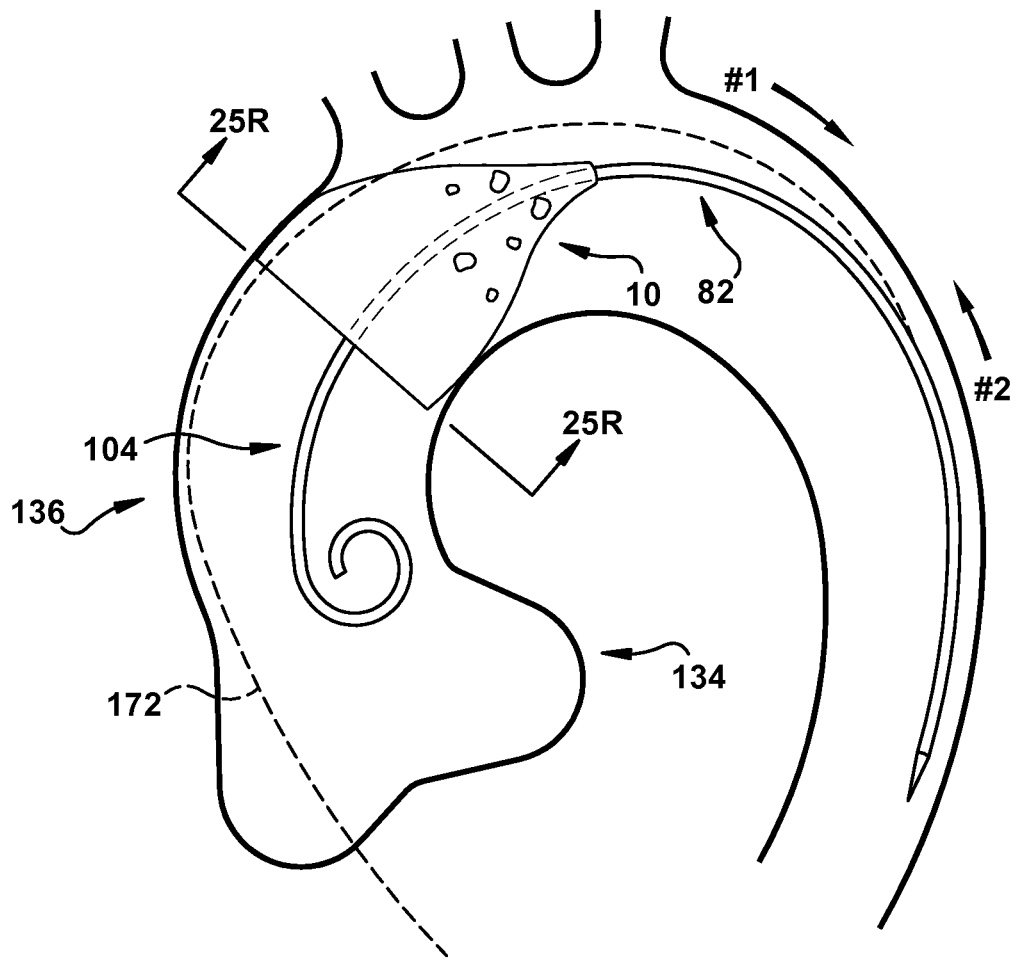
Figure 25R:
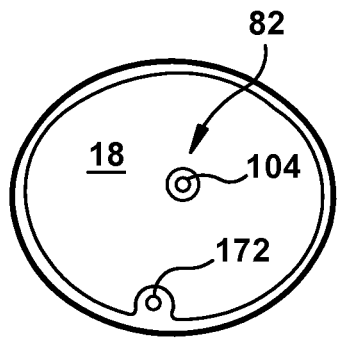
Figure 25S:
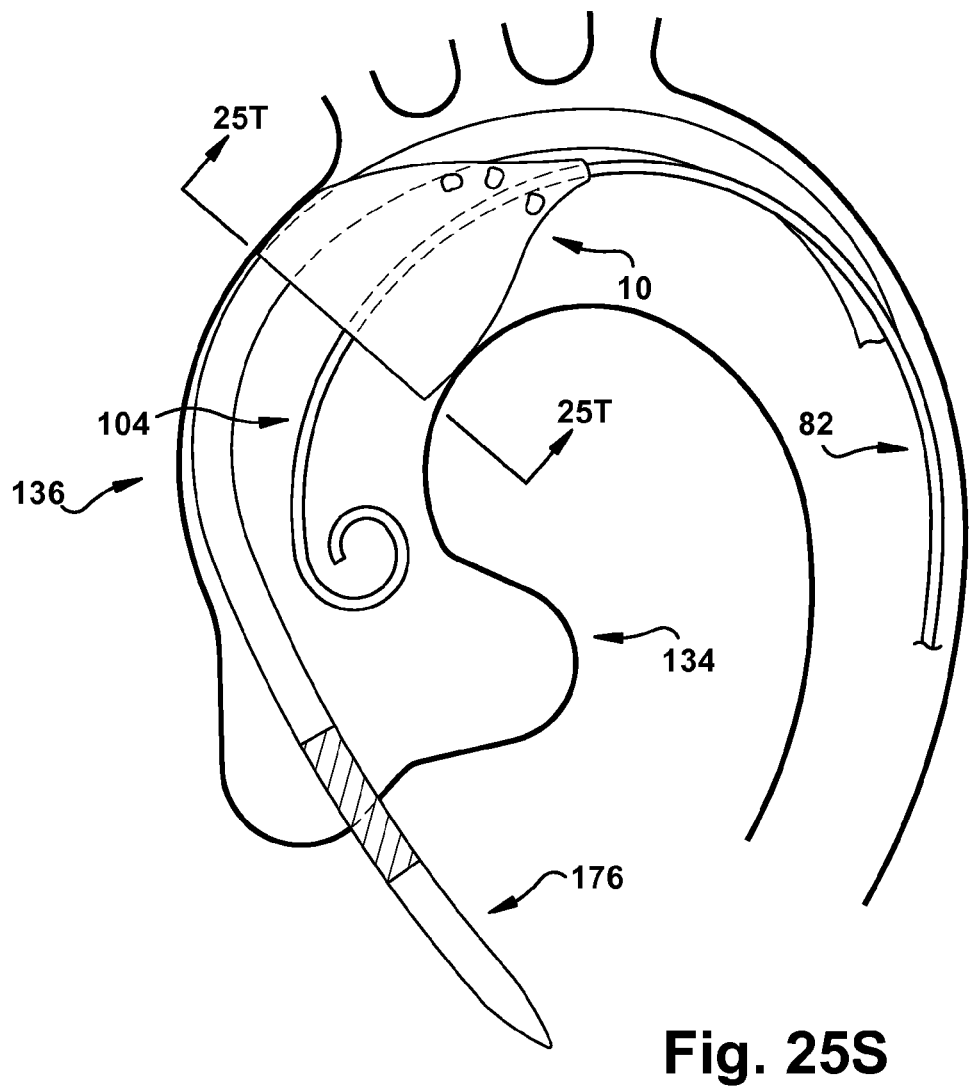
Figure 25T:
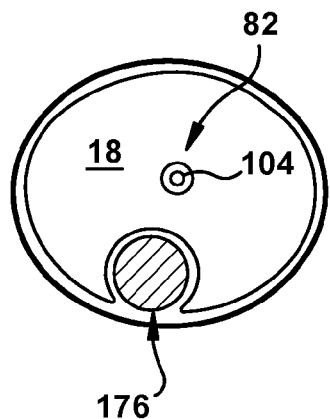

Following deployment of the embolic filter device 10, the pigtail catheter 104 can be slightly withdrawn in preparation for the balloon valvuloplasty procedure. As shown in FIGS. 25O-P, the valvuloplasty procedure can produce emboli (indicated by empty circles) that are then trapped by the membrane 18 of the embolic filter device 18. Advantageously, the position of the BAV 174 in the engaging portion 26 permits the BAV to move or flex during the valvuloplasty procedure without compromising the ability of the embolic filter device 10 to prevent emboli from embolizing in the brain or other vital organs. After the valvuloplasty procedure, the BAV 174 can be removed from the subject (indicated by arrow #1) without having to remove the embolic filter device 10. As shown in FIGS. 25Q-T, an endovascular catheter 28, such as a TAVI catheter 176 can then be advanced through the vasculature and mated with the engaging portion 26 (as described above). With the TAVI catheter 176 appropriately positioned, the medical procedure can then be conducted by replacing (or displacing) the diseased aortic valve 134 with a prosthetic valve 178 (Step 160). During and/or after the procedure, any emboli are captured in the collection chamber 16 of the embolic filter device 10 and thereby prevented from traveling through the aortic arch vessels into the cerebral circulation (FIGS. 25S-T).

Figure 25U:
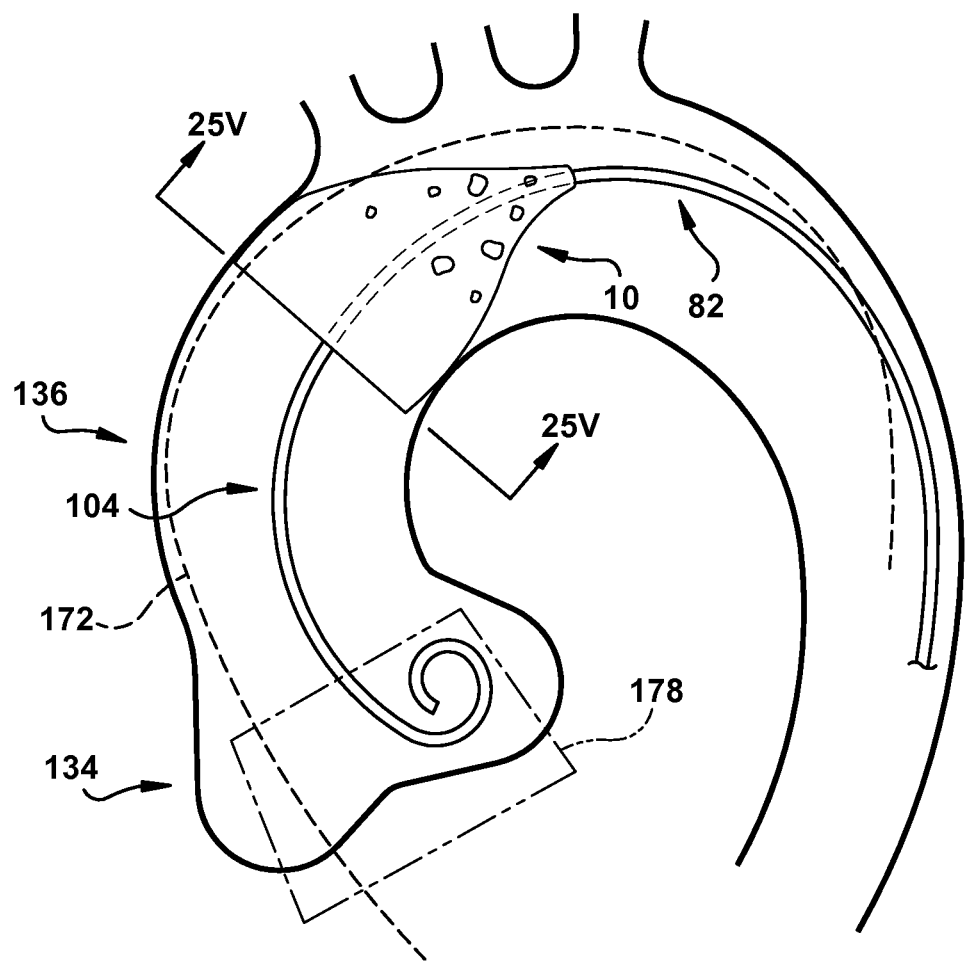
Figure 25V:
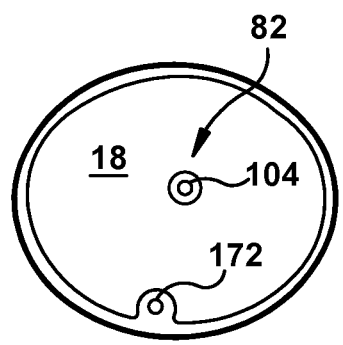
Figure 25W:
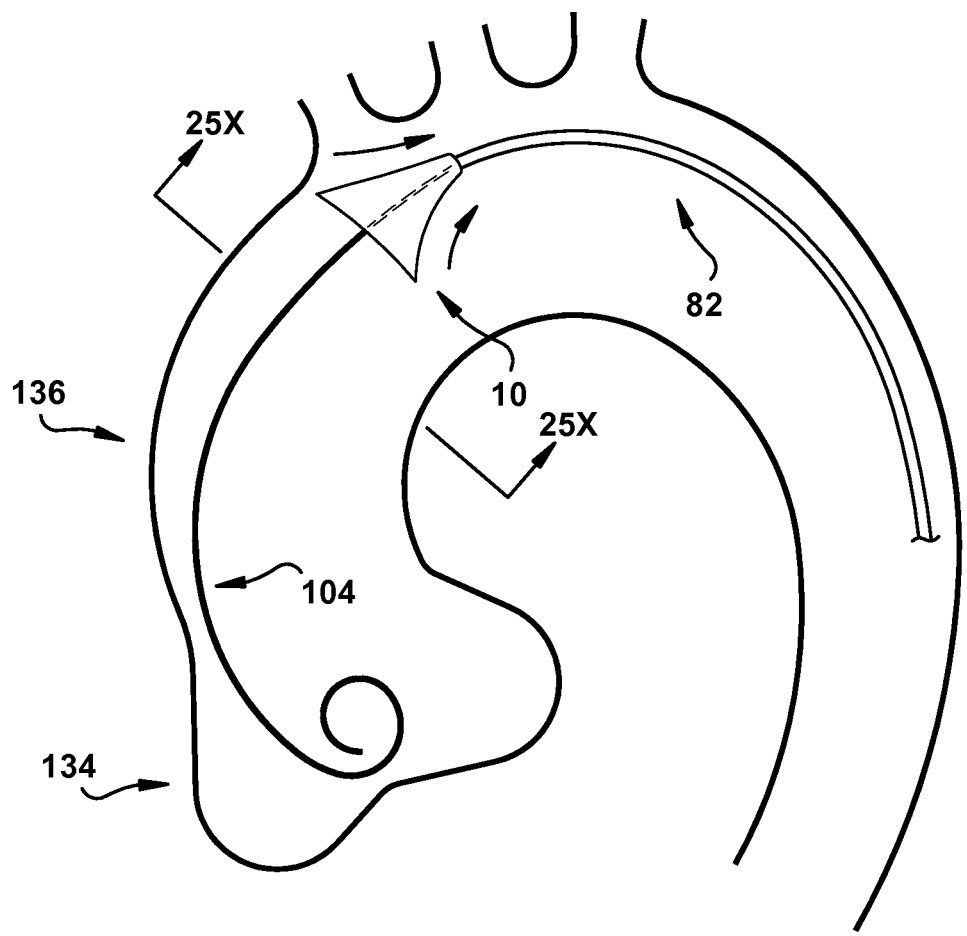
Figure 25X:
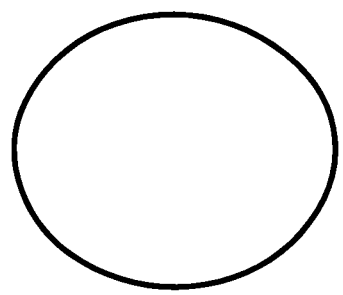

Following the medical procedure, the TAVI catheter 176 can be withdrawn from the subject (FIGS. 25U-V). If needed, the pigtail catheter 104 can be used to assess proper functioning of the prosthetic valve 178. Additionally, if post-dilation is needed, another BAV 174 can be easily introduced over the second guidewire 172. As shown in FIGS. 25W-X, the second guidewire 172 can be removed from the vasculature, followed by collapse and removal of the embolic filter device 10 (indicated by arrows).

Figure 26A:
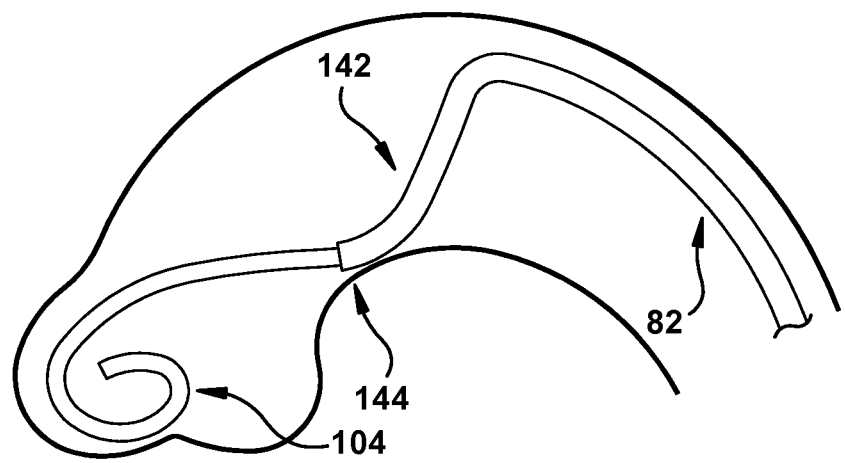
FIGS. 26A-D are a series of perspective views showing an alternative configuration of the intravascular system in FIGS. 19A-B being deployed in an ascending aorta.
Figure 26B:
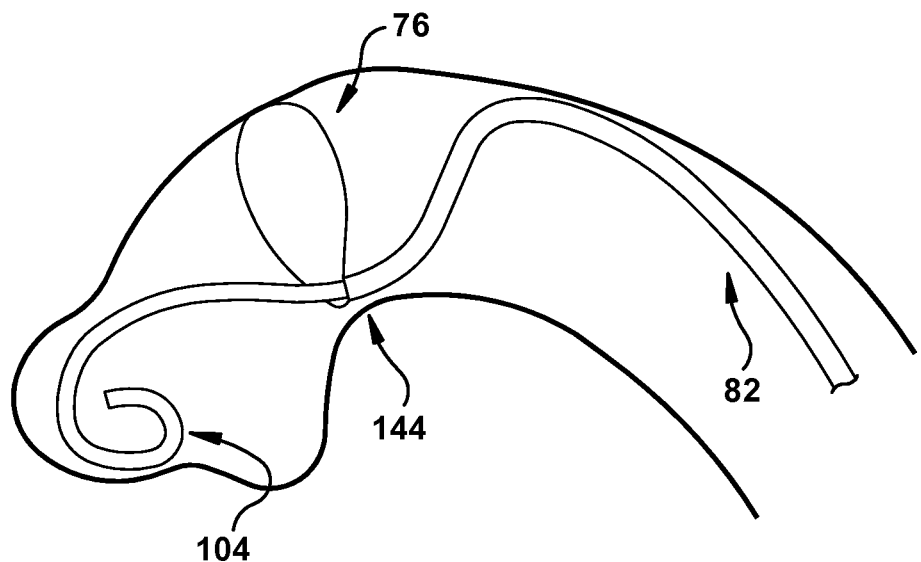

Another aspect of the present disclosure is illustrated in FIGS. 26A-B. As shown in FIG. 26A, the distal end 118 of the multi-lumen delivery catheter 82 can include a pre-shaped section 142 to facilitate deployment of a snare mechanism 72, as well as the embolic filter device 10 about an endovascular catheter 28. In some instances, the pre-shaped section 142 of the multi-lumen delivery catheter 82 can have a sigmoid or S-shaped configuration; however, it will be appreciated that other configurations of the pre-shaped section are possible. With the configuration shown in FIG. 26A, a tip 144 of the multi-lumen delivery catheter 82 is positioned opposite an outer curvature of the ascending aorta 136, while the remaining portion of the multi-lumen delivery catheter is positioned immediately adjacent the outer curvature.

Figure 26C:
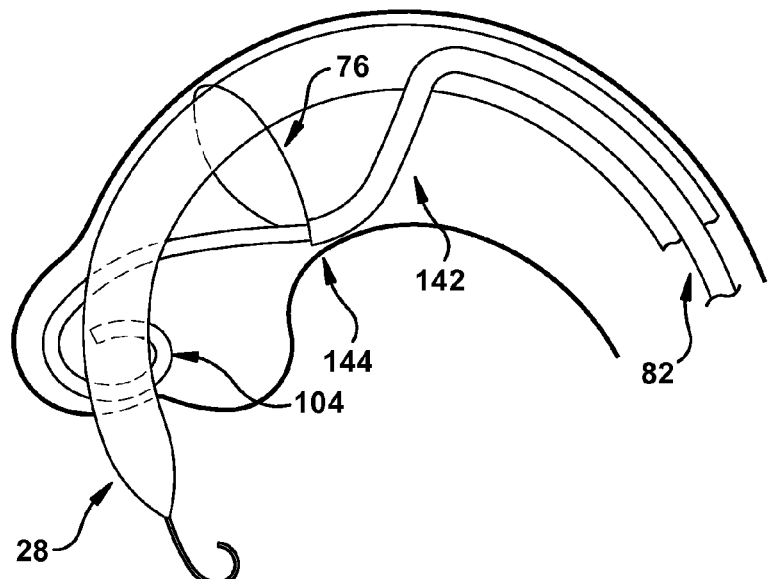
Figure 26D:
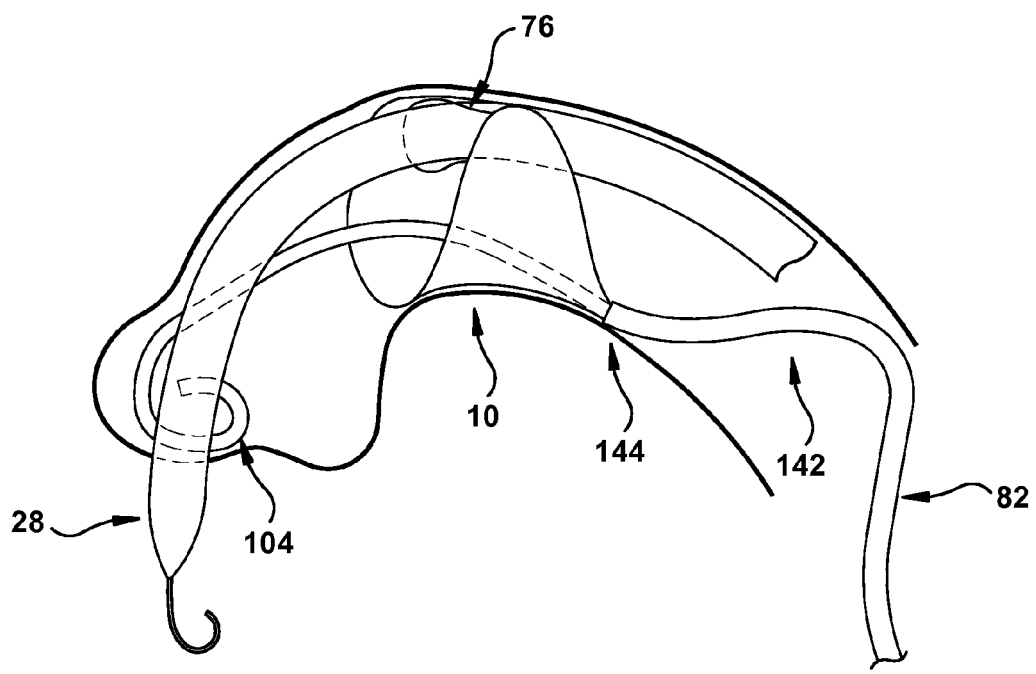

In operation, the multi-lumen delivery catheter 82 can first be positioned as shown in FIG. 26A. With the multi-lumen delivery catheter 82 in place, the pigtail catheter 104 can be deployed from the central lumen 114 of the multi-lumen delivery catheter so that the distal end 98 is adjacent the diseased aortic valve. Next, the lasso portion 76 of the snare mechanism 72 can be progressively advanced out of the multi-lumen delivery catheter 82 towards the outer curvature of the ascending aorta 136 (FIG. 26B). Once the lasso portion 76 is positioned as shown in FIG. 24B, the endovascular catheter 28 can be advanced through the lasso portion (FIG. 26C). Upon threading the endovascular catheter 28 through the lasso portion 76, the embolic filter device 10 can be deployed from the multi-lumen delivery catheter 82. As shown in FIG. 26D, for example, the multi-lumen delivery catheter 82 can be slightly withdrawn to allow the embolic filter device 10 to unfurl about the endovascular catheter 28. The snare mechanism 72 can then be selectively manipulated to cinch the lasso portion 76 and thereby guide the respective portion of the endovascular catheter 28 into the engaging portion 26 of the embolic filter device 10. The medical procedure can then be conducted as described above, ensuring that any emboli captured in the collection chamber 16 of the embolic filter device 10 are prevented from traveling through the aortic arch vessels into the cerebral circulation.

From the above description of the present disclosure, those skilled in the art will perceive improvements, changes and modifications. For example, it will be appreciated that all or only a portion of the embolic filter device 10 may be coated with an anti-thrombogenic coating, such as a bonded heparin coating to reduce the formation of clots that could become potential emboli. Alternatively or in addition, all or only a portion of the embolic filter device 10 may have a drug-eluting coating containing an anti-inflammatory or anti-stenosis agent. Such improvements, changes, and modifications are within the skill of one in the art and are intended to be covered by the appended claims.

The following is claimed:

1. An embolic filter device configured for placement in a blood vessel to capture emboli during a medical procedure, said embolic filter device comprising:
   an expandable frame member including a radial support member operably connected to first and second longitudinal struts and an engaging portion extending between said first and second longitudinal struts, said engaging portion being shaped and configured to temporarily receive, and sealingly mate with, a portion of an endovascular catheter during the medical procedure;
   a membrane securely connected to said frame member and defining a collection chamber for captured emboli, said membrane being configured to cover substantially all of the cross-sectional area of the blood vessel when said embolic filter device is deployed in the blood vessel; and
   a deployable snare mechanism configured to capture the endovascular catheter and selectively mate a portion of the endovascular catheter with said engaging portion, said deployable snare mechanism comprising a lasso portion configured to selectively engage and constrict about an outer surface of the endovascular catheter;
   wherein constriction of said lasso portion causes said lasso portion to twist and cinch about the outer surface of the endovascular catheter such that said engaging portion sealingly mates with the endovascular catheter.

2. The embolic filter device of claim 1, wherein said engaging portion is further defined by a portion of said membrane.

3. The embolic filter device of claim 2, wherein said engaging portion is further defined by a flexible rim, said flexible rim being connected to said radial support member and a portion of said membrane that defines said engaging portion.

4. The embolic filter device of claim 3, wherein said flexible rim obtains an arcuate configuration upon mating with a portion of the endovascular catheter, wherein the flexible rim has a radius of curvature that is substantially similar to a radius of curvature of the portion of the endovascular catheter.

5. The embolic filter device of claim 1, wherein said engaging portion includes a plurality of filamentous members extending between said first and second longitudinal struts.

6. The embolic filter device of claim 1, wherein said radial support member includes at least one bending region configured to facilitate collapse of said expandable frame member into a delivery catheter.

7. The embolic filter device of claim 1, further comprising an integral adjustment mechanism configured to selectively adapt said membrane to cover substantially all of the cross-sectional area of the blood vessel, said integral adjustment mechanism including at least one pullwire that is operably connected to said frame member, wherein application of a longitudinal force to said at least one pullwire translates to a radial force on said radial support member and thereby causes a diameter of said radial support member to transition from a first diameter to a second greater diameter, wherein the second diameter is greater than the first diameter and is about equal to a diameter of the blood vessel.

8. The embolic filter device of claim 1, wherein the medical procedure is transcatheter valve implantation (TAVI).

9. The embolic filter device of claim 1, wherein said embolic filter device obtains a conical shape upon deployment.

10. The embolic filter device of claim 1, wherein said lasso portion is oppositely disposed from said engaging portion.

11. An intravascular system for capturing emboli during a medical procedure, said intravascular system comprising:
   an embolic filter device comprising an expandable frame member, a deployable snare mechanism associated with said expandable frame member, and a membrane securely connected to said frame member and defining a collection chamber for captured emboli, said frame member including a radial support member operably connected to first and second longitudinal struts and an engaging portion extending between said first and second longitudinal struts, said engaging portion being shaped and configured to temporarily receive, and sealingly mate with, a portion of an endovascular catheter during the medical procedure, wherein said deployable snare mechanism is configured to capture the endovascular catheter and selectively mate a portion of the endovascular catheter with said engaging portion, said deployable snare mechanism comprising a lasso portion configured to selectively engage and constrict about an outer surface of the endovascular catheter, wherein constriction of said lasso portion causes said lasso portion to twist and cinch about the outer surface of the endovascular catheter such that said engaging portion sealingly mates with the endovascular catheter; and a multi-lumen delivery catheter having a plurality of lumens, at least one of said lumens being configured to deploy said embolic filter device.

12. The intravascular system of claim 11, wherein said multi-lumen catheter comprises an outer lumen radially disposed about a central lumen, said outer lumen being configured to accommodate said embolic filter device and said central lumen being configured to accommodate a pigtail catheter.

13. A method for capturing emboli during a medical procedure, said method comprising the steps of:

providing an embolic filter device and a multi-lumen delivery catheter, the embolic filter device comprising an expandable frame member, a deployable snare mechanism associated with the expandable frame member, and a membrane securely connected to the frame member and defining a collection chamber for captured emboli, the frame member including a radial support member operably connected to first and second longitudinal struts and an engaging portion extending between the first and second longitudinal struts, the engaging portion being shaped and configured to temporarily receive, and sealingly mate with, a portion of an endovascular catheter during the medical procedure;

advancing the multi-lumen delivery catheter to a deployment site in a blood vessel that is proximate a target location;

deploying a lasso portion of the snare mechanism;

advancing the endovascular catheter to the target location;

threading a portion of the endovascular catheter through the lasso portion;

actuating the snare mechanism to cause the lasso portion to twist and cinch about an outer surface of the endovascular so that the engaging portion is sealingly wrapped around a portion of the endovascular catheter and the membrane covers substantially all of the cross-sectional area of the blood vessel; and conducting the medical procedure.

14. The method of claim 13, wherein the medical procedure is TAVI.

15. The method of claim 13, wherein said step of advancing the multi-lumen delivery catheter further comprises advancing a distal end of the multi-lumen delivery catheter into a portion of an ascending aorta.

16. The method of claim 13, wherein the lasso portion, upon deployment, expands into direct contact with substantially all of the blood vessel wall to allow passage of a medical device therethrough.

17. The method of claim 13, wherein the lasso portion extends at an angle greater than 0° relative to the multi-lumen delivery catheter upon deployment.

* * * * *